US009142141B2

(12) United States Patent  
Yeh et al.

(10) Patent No.: US 9,142,141 B2
(45) Date of Patent: Sep. 22, 2015

(54) DETERMINING EXERCISE ROUTES BASED ON DEVICE DETERMINED INFORMATION

(71) Applicant: SONY CORPORATION, Tokyo (JP)

(72) Inventors: Sabrina Tai-Chen Yeh, Laguna Beach, CA (US); David Andrew Young, San Diego, CA (US); Steven Friedlander, Escondido, CA (US)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/037,276

(22) Filed: Sep. 25, 2013

(65) Prior Publication Data

US 2015/0081209 A1    Mar. 19, 2015

Related U.S. Application Data

(60) Provisional application No. 61/878,835, filed on Sep. 17, 2013.

(51) Int. Cl.  
G01C 21/36 (2006.01)  
G01C 21/34 (2006.01)  
(Continued)

(52) U.S. Cl.  
CPC ............ G09B 19/0038 (2013.01); A61B 5/021 (2013.01); A61B 5/02055 (2013.01); A61B 5/02438 (2013.01); A61B 5/4815 (2013.01); A63B 71/06 (2013.01); G01C 21/00 (2013.01); G01C 21/20 (2013.01); G01S 19/19 (2013.01); G06F 3/017 (2013.01); G06F 3/0481 (2013.01);  
(Continued)

(58) Field of Classification Search  
USPC .............. 701/400, 427–8, 431, 533, 427–428  
See application file for complete search history.

(56) References Cited

U.S. PATENT DOCUMENTS

| 4,278,095 A | 7/1981 | Lapeyre |
| 4,566,461 A | 1/1986 | Lubell et al. |

(Continued)

FOREIGN PATENT DOCUMENTS

| JP | 2009194670 | 8/2009 |
| WO | 2012070019 A2 | 5/2012 |

(Continued)

OTHER PUBLICATIONS

Performtek Sensor Technology, "PerformTek Technology, Monitor Fitness Metrics Using Earbud Sensor Technology" http://www.valencell.com/preformtek-sensor-technology, website printed Sep. 17, 2013.

(Continued)

*Primary Examiner* — Yonel Beaulieu  
(74) *Attorney, Agent, or Firm* — John L. Rogitz

(57) ABSTRACT

A device includes at least one computer readable storage medium bearing instructions executable by a processor and at least one processor configured for accessing the computer readable storage medium to execute the instructions. The instructions configure the processor for accessing terrain information representing preferred terrain of a user of the device, accessing map information, accessing location information indicating current location of the user, and receiving user input indicating a desire for route information. Based at least in part on time constraints indicated from calendar information, the instructions configure the processor for accessing the location information, terrain information, and map information to determine a route and audibly and/or visually displaying the route on the device.

13 Claims, 9 Drawing Sheets

(51) Int. Cl.

| | | |
|---|---|---|
| G09B 19/00 | (2006.01) | |
| G01S 19/19 | (2010.01) | |
| G06F 19/00 | (2011.01) | |
| G06Q 10/06 | (2012.01) | |
| A61B 5/0205 | (2006.01) | |
| A61B 5/021 | (2006.01) | |
| A61B 5/024 | (2006.01) | |
| A61B 5/00 | (2006.01) | |
| A63B 71/06 | (2006.01) | |
| G06F 17/30 | (2006.01) | |
| G06F 3/16 | (2006.01) | |
| H04B 5/00 | (2006.01) | |
| G01C 21/20 | (2006.01) | |
| G06F 3/01 | (2006.01) | |
| G08B 25/01 | (2006.01) | |
| G10L 15/00 | (2013.01) | |
| G01C 21/00 | (2006.01) | |
| G06F 3/0481 | (2013.01) | |
| G06F 3/0484 | (2013.01) | |
| H04L 29/06 | (2006.01) | |
| H04W 4/00 | (2009.01) | |
| H04W 12/08 | (2009.01) | |
| A61B 5/11 | (2006.01) | |
| H04M 1/725 | (2006.01) | |
| A61B 5/117 | (2006.01) | |
| A61B 5/145 | (2006.01) | |

(52) U.S. Cl.
CPC .............. *G06F 3/0484* (2013.01); *G06F 3/165* (2013.01); *G06F 17/3074* (2013.01); *G06F 19/3481* (2013.01); *G06Q 10/0639* (2013.01); *G08B 25/016* (2013.01); *G10L 15/00* (2013.01); *H04B 5/0025* (2013.01); *H04L 63/0853* (2013.01); *H04W 4/008* (2013.01); *H04W 12/08* (2013.01); *A61B 5/11* (2013.01); *A61B 5/1172* (2013.01); *A61B 5/1176* (2013.01); *A61B 5/14532* (2013.01); *A61B 5/14542* (2013.01); *H04M 1/7253* (2013.01); *H04M 2250/02* (2013.01); *H04M 2250/04* (2013.01); *H04M 2250/12* (2013.01)

(56) References Cited

U.S. PATENT DOCUMENTS

| | | |
|---|---|---|
| 4,625,962 A | 12/1986 | Street |
| 4,708,337 A | 11/1987 | Shyu |
| 4,728,100 A | 3/1988 | Smith |
| 4,869,497 A | 9/1989 | Stewart et al. |
| 4,916,628 A | 4/1990 | Kugler |
| 4,920,969 A | 5/1990 | Suzuki et al. |
| 5,072,458 A | 12/1991 | Suzuki |
| 5,111,818 A | 5/1992 | Suzuki et al. |
| 5,207,621 A | 5/1993 | Koch et al. |
| 5,277,197 A | 1/1994 | Church et al. |
| 5,314,389 A | 5/1994 | Dotan |
| 5,410,472 A | 4/1995 | Anderson |
| 5,433,683 A | 7/1995 | Stevens |
| 5,454,770 A | 10/1995 | Stevens |
| 5,474,083 A | 12/1995 | Church et al. |
| 5,474,090 A | 12/1995 | Begun et al. |
| 5,516,334 A | 5/1996 | Easton |
| 5,524,637 A | 6/1996 | Erickson |
| 5,579,777 A | 12/1996 | Suga |
| 5,598,849 A | 2/1997 | Browne |
| 5,704,067 A | 1/1998 | Brady |
| 5,706,822 A | 1/1998 | Khavari |
| 5,857,939 A | 1/1999 | Kaufman |
| 5,921,891 A | 7/1999 | Browne |
| 6,013,007 A | 1/2000 | Root et al. |
| 6,032,108 A | 2/2000 | Seiple et al. |
| 6,042,519 A | 3/2000 | Shea |
| 6,050,924 A | 4/2000 | Shea |
| 6,106,297 A | 8/2000 | Pollak et al. |
| 6,171,218 B1 | 1/2001 | Shea |
| 6,198,431 B1 | 3/2001 | Gibson |
| 6,220,865 B1 | 4/2001 | Macri et al. |
| 6,244,988 B1 | 6/2001 | Delman |
| 6,251,048 B1 | 6/2001 | Kaufman |
| 6,259,944 B1 | 7/2001 | Margulis et al. |
| 6,296,595 B1 | 10/2001 | Stark et al. |
| 6,447,425 B1 | 9/2002 | Keller et al. |
| 6,464,618 B1 | 10/2002 | Shea |
| 6,497,638 B1 | 12/2002 | Shea |
| 6,500,100 B1 | 12/2002 | Harrell |
| 6,515,593 B1 | 2/2003 | Stark et al. |
| 6,582,342 B2 | 6/2003 | Kaufman |
| 6,601,016 B1 | 7/2003 | Brown et al. |
| 6,605,044 B2 | 8/2003 | Bimbaum |
| 6,638,198 B1 | 10/2003 | Shea |
| 6,659,916 B1 | 12/2003 | Shea |
| 6,659,946 B1 | 12/2003 | Batchelor et al. |
| 6,672,991 B2 | 1/2004 | O'Malley |
| 6,702,719 B1 | 3/2004 | Brown et al. |
| 6,746,371 B1 | 6/2004 | Brown et al. |
| 6,749,537 B1 | 6/2004 | Hickman |
| 6,786,848 B2 | 9/2004 | Yamashita et al. |
| 6,793,607 B2 | 9/2004 | Neil |
| 6,863,641 B1 | 3/2005 | Brown et al. |
| 6,866,613 B1 | 3/2005 | Brown et al. |
| 6,882,883 B2 | 4/2005 | Condie et al. |
| 6,997,882 B1 | 2/2006 | Parker et al. |
| 7,024,369 B1 | 4/2006 | Brown et al. |
| 7,056,265 B1 | 6/2006 | Shea |
| 7,057,551 B1 | 6/2006 | Vogt |
| 7,070,539 B2 | 7/2006 | Brown et al. |
| 7,128,693 B2 | 10/2006 | Brown et al. |
| 7,192,401 B2 | 3/2007 | Salaasti et al. |
| 7,223,215 B2 | 5/2007 | Bastyr |
| 7,227,468 B1 | 6/2007 | Florio |
| 7,245,254 B1 | 7/2007 | Vogt |
| 7,328,612 B2 | 2/2008 | Jämsen et al. |
| 7,351,187 B2 | 4/2008 | Seliber |
| 7,370,763 B1 | 5/2008 | Pascucci |
| 7,376,423 B2 | 5/2008 | Sakanaba |
| 7,438,670 B2 | 10/2008 | Gray et al. |
| 7,507,183 B2 | 3/2009 | Anderson et al. |
| 7,586,418 B2 | 9/2009 | Cuddihy et al. |
| 7,617,615 B1 | 11/2009 | Martorell et al. |
| 7,633,076 B2 | 12/2009 | Huppi et al. |
| 7,664,292 B2 | 2/2010 | Van Den et al. |
| 7,683,252 B2 | 3/2010 | Oliver et al. |
| 7,699,752 B1 | 4/2010 | Anderson et al. |
| 7,728,214 B2 | 6/2010 | Oliver et al. |
| 7,786,856 B2 | 8/2010 | O'Brien |
| 7,840,031 B2 | 11/2010 | Albertson et al. |
| 7,841,966 B2 | 11/2010 | Aaron et al. |
| 7,857,730 B2 | 12/2010 | Dugan |
| 7,931,563 B2 | 4/2011 | Shaw et al. |
| 7,951,046 B1 | 5/2011 | Barber, Jr. |
| 7,966,230 B2 | 6/2011 | Brown |
| 7,979,136 B2 | 7/2011 | Young et al. |
| 7,996,080 B1 | 8/2011 | Hartman et al. |
| 8,021,270 B2 | 9/2011 | D'eredita |
| 8,029,410 B2 | 10/2011 | Shea |
| 8,047,965 B2 | 11/2011 | Shea |
| 8,057,360 B2 | 11/2011 | Shea |
| 8,062,182 B2 | 11/2011 | Somers |
| 8,092,346 B2 | 1/2012 | Shea |
| 8,103,762 B2 | 1/2012 | Duberry |
| 8,109,858 B2 | 2/2012 | Redmann |
| 8,157,730 B2 | 4/2012 | LeBoeuf et al. |
| 8,162,802 B2 | 4/2012 | Berg |
| 8,182,424 B2 | 5/2012 | Heckerman |
| 8,199,014 B1 | 6/2012 | Kindeberg |
| 8,204,786 B2 | 6/2012 | LeBoeuf et al. |
| 8,219,191 B1 | 7/2012 | Hartman et al. |
| 8,277,377 B2 | 10/2012 | Quy |
| 8,317,658 B2 | 11/2012 | Dorogusker et al. |

(56) References Cited

U.S. PATENT DOCUMENTS

| | | |
|---|---|---|
| 8,333,874 B2 | 12/2012 | Currie |
| 8,343,012 B2 | 1/2013 | Redmann |
| 8,360,785 B2 | 1/2013 | Park et al. |
| 8,360,935 B2 | 1/2013 | Olsen et al. |
| 8,371,990 B2 | 2/2013 | Shea |
| 8,406,085 B2 | 3/2013 | Sakita |
| 8,435,177 B2 | 5/2013 | Lanfermann et al. |
| 8,452,413 B2 | 5/2013 | Young et al. |
| 8,467,860 B2 | 6/2013 | Salazar et al. |
| 8,491,446 B2 | 7/2013 | Hinds et al. |
| 8,512,209 B2 | 8/2013 | Guidi et al. |
| 8,512,548 B2 | 8/2013 | Bar-or et al. |
| 8,514,067 B2 | 8/2013 | Hyde et al. |
| 8,597,093 B2 * | 12/2013 | Engelberg et al. ............... 463/1 |
| 8,795,138 B1 | 8/2014 | Yeh et al. |
| 8,825,445 B2 | 9/2014 | Hoffman et al. |
| 2001/0020143 A1 | 9/2001 | Stark et al. |
| 2002/0028730 A1 | 3/2002 | Kaufman |
| 2002/0072932 A1 | 6/2002 | Swamy |
| 2002/0082142 A1 | 6/2002 | Cannon et al. |
| 2002/0108000 A1 | 8/2002 | Iori et al. |
| 2002/0142887 A1 | 10/2002 | O'Malley |
| 2002/0156392 A1 | 10/2002 | Arai et al. |
| 2003/0028116 A1 | 2/2003 | Birnbaum |
| 2003/0064860 A1 | 4/2003 | Yamashita et al. |
| 2003/0171188 A1 | 9/2003 | Neil |
| 2003/0171189 A1 | 9/2003 | Kaufman |
| 2004/0058908 A1 | 3/2004 | Keller et al. |
| 2004/0077462 A1 | 4/2004 | Brown et al. |
| 2004/0117214 A1 | 6/2004 | Shea |
| 2005/0070809 A1 | 3/2005 | Acres |
| 2005/0075214 A1 | 4/2005 | Brown et al. |
| 2005/0163346 A1 | 7/2005 | Van Den et al. |
| 2005/0177059 A1 | 8/2005 | Koivumaa et al. |
| 2005/0209002 A1 | 9/2005 | Blythe et al. |
| 2005/0233861 A1 | 10/2005 | Hickman et al. |
| 2005/0272561 A1 | 12/2005 | Cammerata |
| 2006/0020216 A1 | 1/2006 | Oishi et al. |
| 2006/0025282 A1 | 2/2006 | Redmann |
| 2006/0032315 A1 | 2/2006 | Saalastic et al. |
| 2006/0058156 A1 | 3/2006 | Cohen et al. |
| 2006/0094570 A1 | 5/2006 | Schneider |
| 2006/0111944 A1 | 5/2006 | Sirmans, Jr. et al. |
| 2006/0113381 A1 | 6/2006 | Hochstein et al. |
| 2006/0240959 A1 | 10/2006 | Huang |
| 2006/0252602 A1 | 11/2006 | Brown et al. |
| 2006/0281976 A1 | 12/2006 | Juang et al. |
| 2006/0288846 A1 | 12/2006 | Logan |
| 2007/0033068 A1 | 2/2007 | Rao et al. |
| 2007/0033069 A1 | 2/2007 | Rao et al. |
| 2007/0042868 A1 | 2/2007 | Fisher et al. |
| 2007/0083092 A1 | 4/2007 | Rippo et al. |
| 2007/0083095 A1 | 4/2007 | Rippo et al. |
| 2007/0113725 A1 | 5/2007 | Oliver et al. |
| 2007/0113726 A1 | 5/2007 | Oliver et al. |
| 2007/0173377 A1 | 7/2007 | Jamsen et al. |
| 2007/0213608 A1 | 9/2007 | Brown |
| 2007/0219059 A1 | 9/2007 | Schwartz et al. |
| 2007/0249467 A1 | 10/2007 | Hong et al. |
| 2007/0249468 A1 | 10/2007 | Chen |
| 2007/0266065 A1 | 11/2007 | Rosenberg |
| 2007/0275825 A1 | 11/2007 | O'Brien |
| 2007/0300185 A1 | 12/2007 | Macbeth et al. |
| 2008/0045384 A1 | 2/2008 | Matsubara et al. |
| 2008/0051919 A1 | 2/2008 | Sakai et al. |
| 2008/0098876 A1 | 5/2008 | Kuo et al. |
| 2008/0103022 A1 | 5/2008 | Dvorak et al. |
| 2008/0146890 A1 | 6/2008 | Leboeuf et al. |
| 2008/0146892 A1 | 6/2008 | LeBoeuf et al. |
| 2008/0147502 A1 | 6/2008 | Baker |
| 2008/0153670 A1 | 6/2008 | McKirdy et al. |
| 2008/0162186 A1 | 7/2008 | Jones |
| 2008/0170123 A1 | 7/2008 | Albertson et al. |
| 2008/0176713 A1 | 7/2008 | Olivera |
| 2008/0182723 A1 | 7/2008 | Aaron et al. |
| 2008/0204225 A1 | 8/2008 | Kitchen |
| 2008/0220941 A1 | 9/2008 | Shaw et al. |
| 2008/0262918 A1 | 10/2008 | Wiener |
| 2009/0044687 A1 | 2/2009 | Sorber |
| 2009/0105047 A1 | 4/2009 | Guidi et al. |
| 2009/0131224 A1 | 5/2009 | Yuen |
| 2009/0131759 A1 | 5/2009 | Sims et al. |
| 2009/0138488 A1 | 5/2009 | Shea |
| 2009/0149131 A1 | 6/2009 | Young et al. |
| 2009/0150175 A1 | 6/2009 | Young et al. |
| 2009/0233771 A1 | 9/2009 | Quatrochi et al. |
| 2009/0247366 A1 | 10/2009 | Frumer |
| 2009/0247368 A1 | 10/2009 | Chiang |
| 2009/0258758 A1 | 10/2009 | Hickman et al. |
| 2009/0275442 A1 | 11/2009 | Nissila |
| 2009/0287103 A1 | 11/2009 | Pillai |
| 2009/0292178 A1 | 11/2009 | Ellis et al. |
| 2009/0293298 A1 | 12/2009 | Martorell et al. |
| 2009/0298426 A1 | 12/2009 | Helvick |
| 2010/0017114 A1 * | 1/2010 | Tehan et al. ............... 701/202 |
| 2010/0035726 A1 | 2/2010 | Fisher et al. |
| 2010/0056341 A1 | 3/2010 | Ellis et al. |
| 2010/0120585 A1 | 5/2010 | Quy |
| 2010/0134257 A1 | 6/2010 | Puleston et al. |
| 2010/0167876 A1 | 7/2010 | Cheng |
| 2010/0186078 A1 | 7/2010 | Napoli et al. |
| 2010/0190607 A1 | 7/2010 | Widerman et al. |
| 2010/0216603 A1 | 8/2010 | Somers |
| 2010/0217099 A1 | 8/2010 | LeBoeuf et al. |
| 2010/0222178 A1 | 9/2010 | Shea |
| 2010/0222181 A1 | 9/2010 | Shea |
| 2010/0234699 A1 | 9/2010 | Lanfermann et al. |
| 2010/0273610 A1 | 10/2010 | Johnson |
| 2011/0001827 A1 | 1/2011 | Ortiz et al. |
| 2011/0015039 A1 | 1/2011 | Shea |
| 2011/0015041 A1 | 1/2011 | Shea |
| 2011/0035184 A1 | 2/2011 | Aaron et al. |
| 2011/0059825 A1 | 3/2011 | Mcgown |
| 2011/0098112 A1 | 4/2011 | LeBoeuf et al. |
| 2011/0098583 A1 | 4/2011 | Pandia et al. |
| 2011/0106627 A1 | 5/2011 | LeBoeuf et al. |
| 2011/0137191 A1 | 6/2011 | Kinnunen |
| 2011/0165996 A1 | 7/2011 | Paulus et al. |
| 2011/0165998 A1 | 7/2011 | Lav et al. |
| 2011/0179068 A1 | 7/2011 | O'Brien |
| 2011/0195780 A1 | 8/2011 | Lu |
| 2011/0195819 A1 | 8/2011 | Shaw et al. |
| 2011/0205697 A1 * | 8/2011 | Callicoat et al. ......... 361/679.01 |
| 2011/0212688 A1 | 9/2011 | Griffin et al. |
| 2011/0230142 A1 | 9/2011 | Young et al. |
| 2011/0246908 A1 | 10/2011 | Akram et al. |
| 2011/0263385 A1 | 10/2011 | Shea et al. |
| 2011/0275042 A1 | 11/2011 | Warman et al. |
| 2011/0288381 A1 | 11/2011 | Bartholomew et al. |
| 2011/0319228 A1 | 12/2011 | Shea |
| 2012/0010478 A1 | 1/2012 | Kinnunen et al. |
| 2012/0058859 A1 | 3/2012 | Elsom-Cook et al. |
| 2012/0077580 A1 | 3/2012 | Mahajan et al. |
| 2012/0108395 A1 | 5/2012 | Shea |
| 2012/0129138 A1 | 5/2012 | Redmann |
| 2012/0142429 A1 | 6/2012 | Muller |
| 2012/0178431 A1 | 7/2012 | Gold |
| 2012/0184871 A1 | 7/2012 | Jang et al. |
| 2012/0190502 A1 | 7/2012 | Paulus et al. |
| 2012/0203081 A1 | 8/2012 | LeBoeuf et al. |
| 2012/0226111 A1 | 9/2012 | LeBoeuf et al. |
| 2012/0226112 A1 | 9/2012 | LeBoeuf et al. |
| 2012/0271913 A1 | 10/2012 | Tallgren et al. |
| 2013/0032634 A1 | 2/2013 | McKirdy |
| 2013/0046477 A1 | 2/2013 | Hyde et al. |
| 2013/0089842 A1 | 4/2013 | Shea |
| 2013/0090213 A1 | 4/2013 | Amini et al. |
| 2013/0090565 A1 | 4/2013 | Quy |
| 2013/0095459 A1 | 4/2013 | Tran |
| 2013/0110265 A1 | 5/2013 | Rahko et al. |
| 2013/0130213 A1 | 5/2013 | Burbank et al. |
| 2013/0155251 A1 | 6/2013 | Moravchik |
| 2013/0178960 A1 | 7/2013 | Sheehan et al. |
| 2013/0217541 A1 | 8/2013 | Shea |

(56) References Cited

U.S. PATENT DOCUMENTS

| | | | |
|---|---|---|---|
| 2013/0217542 A1 | 8/2013 | Shea | |
| 2013/0217543 A1 | 8/2013 | Shea | |
| 2013/0218309 A1 | 8/2013 | Napolitano | |
| 2013/0225369 A1 | 8/2013 | Fisbein et al. | |
| 2013/0304377 A1* | 11/2013 | Van Hende | 701/533 |
| 2013/0308192 A1 | 11/2013 | Shimoda | |
| 2013/0325326 A1* | 12/2013 | Blumenberg et al. | 701/428 |
| 2014/0000322 A1 | 1/2014 | Williams | |
| 2014/0124570 A1 | 5/2014 | Franklin | |
| 2014/0248996 A1 | 9/2014 | Adel | |
| 2015/0081210 A1* | 3/2015 | Yeh et al. | 701/428 |

FOREIGN PATENT DOCUMENTS

| | | |
|---|---|---|
| WO | 2012176193 | 12/2012 |
| WO | 2013055380 | 4/2013 |

OTHER PUBLICATIONS

Steve Silverman, "Biometic Exercises" http://www.livestrong.com/article/282962-biometrics-exercises/, Mar. 31, 2011.

Julie Anne Framel, Aravind Babu Asam, Guru Prashanth Balasubramanian, Takeshi Suzuki, Charles D. Hedrick Jr.; "User Device Position Indication for Security and Distributed Race Challenges" related U.S. Appl. No. 13/644,044 non-final office action dated Apr. 14, 2014.

Julie Anne Framel, Aravind Babu Asam, Guru Prashanth Balasubramanian, Takeshi Suzuki, Charles D. Hedrick Jr.; "User Device Position Indication for Security and Distributed Race Challenges" related U.S. Appl. No. 13/644,044 applicants response to non-final office action filed Apr. 24, 2014.

Sabrina Tai-Chen Yeh, Jenny Therese Fredriksson, "Combining Data Sources to Provide Accurate Effort Monitoring" related U.S. Appl. No. 14/255,663 non-final office action dated Sep. 12, 2014.

Sabrina Tai-Chen Yeh, Jenny Therese Fredriksson, "Combining Data Sources to Provide Accurate Effort Monitoring" related U.S. Appl. No. 14/255,663 applicants response to the non-final office action filed Oct. 30, 2014.

Judith A. Markowitz, "Voice Biometrics, Who Are You? Your voice along can be used to verify your personal identity—unobtrusively and invisibly." Sep. 2000/ vol. 43. No. 9, Communications of the ACM. http://www.web2.utc.edu/~djy471/documents/voice-biometrics-p66-markowitz.pdf.

Veli-Jussi Raitila, "Tag, you're it—NFC in a home environment" TKK T-110.5190 Seminar on Internertworking, Finland, pp. 1-6, 2007. http://www.tml.tkk.fi/Publications/C/23/papers/Raitila_final.pdf.

Julia Anne Framel, Aravind Babu Asam, Guru Prashanth Balasubramanian, Takeshi Suzuki, Charles D. Hedrick Jr., "User Device Position Indication for Security and Distributed Race Challenges", File History of related U.S. Appl. No. 13/644,044, filed Oct. 3, 2012.

Sabrina Tai-Chen Yeh, David Andrew Young, "Altering Exercise Routes Based on Device Determined Information", file history of related U.S. Appl. No. 14/037,286, filed Sep. 25, 2013.

Sabrina Tai-Chen Yeh, Steven Friedlander, David Andrew Young, "Nonverbal Audio Cues During Physical Activity", file history of related U.S. Appl. No. 14/037,278, filed Sep. 25, 2013.

Sabrina Tai-Chen Yeh, Takashi Hironaka, David Andrew Young, Steven Friedlander, "Quick Login to User Profile on Exercise Machine", file history of related U.S. Appl. No. 14/037,263, filed Sep. 25, 2013.

Sabrina Ta-Chen Yeh, Steven Friedlander, David Andrew Young, "Synchronized Exercise Buddy Headphones", file history of related U.S. Appl. No. 14/037,267, filed Sep. 25, 2013.

Sabrina Tai-Chen Yeh, David Andrew Young, Takashi Hironaka, Steven Friedlander, "Presenting Audio Based on Biometrics Parameters", file history of related U.S. Appl. No. 14/037,271, filed Sep. 25, 2013.

Sabrina Tai-Chen Yeh, Steven Friedlander, David Andrew Young, "Presenting Audio Video on Biometrics Parameters", file history of related U.S. Appl. No. 14/037,252, filed Sep. 25, 2013.

Sabrina Tai-Chen Yeh, Jenny Therese Fredriksson, "Combining Data Sources to Provide Accurate Effort Monitoring", file history of related U.S. Appl. No. 14/037,224, filed Sep. 25, 2013.

Sabrina Tai-Chen Yeh, Jenny Therese Fredriksson, "Intelligent Device Mode Shifting Based on Activity", file history of related U.S. Appl. No. 14/037,228, filed Sep. 25, 2013.

Jason Michael Warner, "Devices and Methods for Health Tracking and Providing Information for Improving Health", file history of related U.S. Appl. No. 14/160,871, filed Jan. 22, 2014.

Julia Anne Framel, Aravind Babu Asam, Guru Prashanth BALASUBRAMANiAN, Takeshi Suzuki, Charles D. Hendrick, "User Device Position Indication for Security and Distributed Race Challenges", related U.S. Appl. No. 14/261,075. Non-Final Office Action dated Mar. 23, 2015.

Sabrina Tai-Chen Yeh, Takashi Hironaka, David Andrew Young, Steven Friedlander, "Quick Login to User Profile on Exercise Machine", related U.S. Appl. No. 14/037,263, Non-Final Office Action dated May 27, 2015.

Sabrina Tai-Chen Yeh, Takashi Hironaka, David Andrew Young, Steven Friedlander, "Quick Login to User Profile on Exercise Machine", related U.S. Appl. No. 14/037,263, Applicant's response to Non-Final Office Action dated May 29, 2015.

\* cited by examiner

Plan Your Route:

| | | |
|---|---|---|
| | | 181 — Select Past Route |
| | | 183 — See Friend's Routes |
| Distance: | ☐ 162 | |
| Total Time: | ☐ 164 | |
| Start Location: | ☐ 166 | See Map — 168 |
| End Location: | ☐ 170 | See Map — 172 |
| Maximum Distance from Start: | ☐ 174 | |
| Difficulty Level: | ☐ 176 | |
| Terrain: | ☐ 180 | More Specific — 178 |
| Fitness Level: | ☐ 182 | 184 — Submit |

*FIG. 5*

Plan Desired Terrain:

For: ☐ 188 minutes, ☐ 190 terrain; then

For: ☐ 188 minutes, ☐ 190 terrain; then

For: ☐ 188 minutes, ☐ 190 terrain.

192 — Submit

*FIG. 6*

DETERMINING EXERCISE ROUTES BASED ON DEVICE DETERMINED INFORMATION

This application claims priority to U.S. provisional patent application Ser. No. 61/878,835, filed Sep. 17, 2013.

FIELD OF THE INVENTION

The present application relates generally to digital ecosystems that are configured for use when engaging in physical activity and/or fitness exercises.

BACKGROUND OF THE INVENTION

Society is becoming increasingly health-conscious. A wide variety of exercise and workouts are now offered to encourage people to stay fit through exercise. As understood herein, while stationary exercise equipment often comes equipped with data displays for the information of the exerciser, the information is not tailored to the individual and is frequently repetitive and monotonous. As further understood herein, people enjoy listening to music as workout aids but the music typically is whatever is broadcast within a gymnasium or provided on a recording device the user may wear, again being potentially monotonous and unchanging in pattern and beat in a way that is uncoupled from the actual exercise being engaged in.

Thus, while present principles recognize that consumer electronics (CE) devices may be used while engaged in physical activity to enhance the activity, most audio and/or visual aids are static in terms of not being tied to the actual exercise.

SUMMARY OF THE INVENTION

Present principles recognize that portable aids can be provided to improve exercise performance, provide inspiration, enable the sharing of exercise performance for social reasons, help fulfill a person's exercise goals, analyze and track exercise results, and provide virtual coaching to exercise participants in an easy, intuitive manner.

Accordingly, in a first aspect a device includes at least one computer readable storage medium bearing instructions executable by a processor and at least one processor configured for accessing the computer readable storage medium to execute the instructions. The instructions configure the processor for accessing terrain information representing preferred terrain of a user of the device, accessing map information, accessing location information indicating current location of the user, and receiving user input indicating a desire for route information. Based at least in part on time constraints indicated from calendar information, the instructions configure the processor for accessing the location information, terrain information, and map information to determine a route and audibly and/or visually displaying the route on the device.

If desired, the user input may include voice input and/or a hand gesture in free space. Furthermore, in some embodiments the processor when executing the instructions may be further configured for accessing fitness information pertaining to a fitness level of the user and using the fitness information to determine the route. Also in some embodiments, the processor when executing the instructions may be further configured for accessing personal preference information pertaining to preferences of a user of the device and using the preference information to determine a route. Further still, if desired the processor when executing the instructions may be further configured for outputting a distance and a time to complete associated with the route, and/or determining the route by determining an initial route and determining plural circuits of the initial route, where the plural circuits of the initial route establish the route to satisfy the user input indicating a desire for route information while remaining within time and/or personal preference constraints of the user.

In another aspect, a method includes receiving input from a user of a first consumer electronics (CE) device indicating a desired distance for a travel route, a starting location for the travel route, and an ending location for the travel route. The method also includes determining a travel route based on the input and presenting a graphical user interface (GUI) on the first CE device representing a map of the travel route.

In still another aspect, a server includes at least one computer readable storage medium bearing instructions executable by a processor and at least one processor configured for accessing the computer readable storage medium to execute the instructions. The instructions configure the processor to communicate with at least first and second consumer electronics (CE) devices to at least determine the location of at least one of the first and second CE devices, and provide to the first and second CE devices information pertaining to a route for respective users of the first and second CE devices to travel, where the route being based at least on at least one current climate parameter of the climate at or around the location of at least one of the CE devices, at least one temporal parameter, and at least one distance parameter. The instructions also configure the processor to receive real time location updates from each of the first and second CE devices as the first and second CE devices move along the route and provide to at least the first CE device information pertaining to the real time location at least of the second CE device as the second CE device moves along the route.

The details of the present invention, both as to its structure and operation, can best be understood in reference to the accompanying drawings, in which like reference numerals refer to like parts, and in which:

BRIEF DESCRIPTION OF THE DRAWINGS

FIGS. 5-11 are example user interfaces (UIs) for presenting route information and/or determining routes in accordance with present principles.

DETAILED DESCRIPTION OF THE PREFERRED EMBODIMENT

Figure 1:
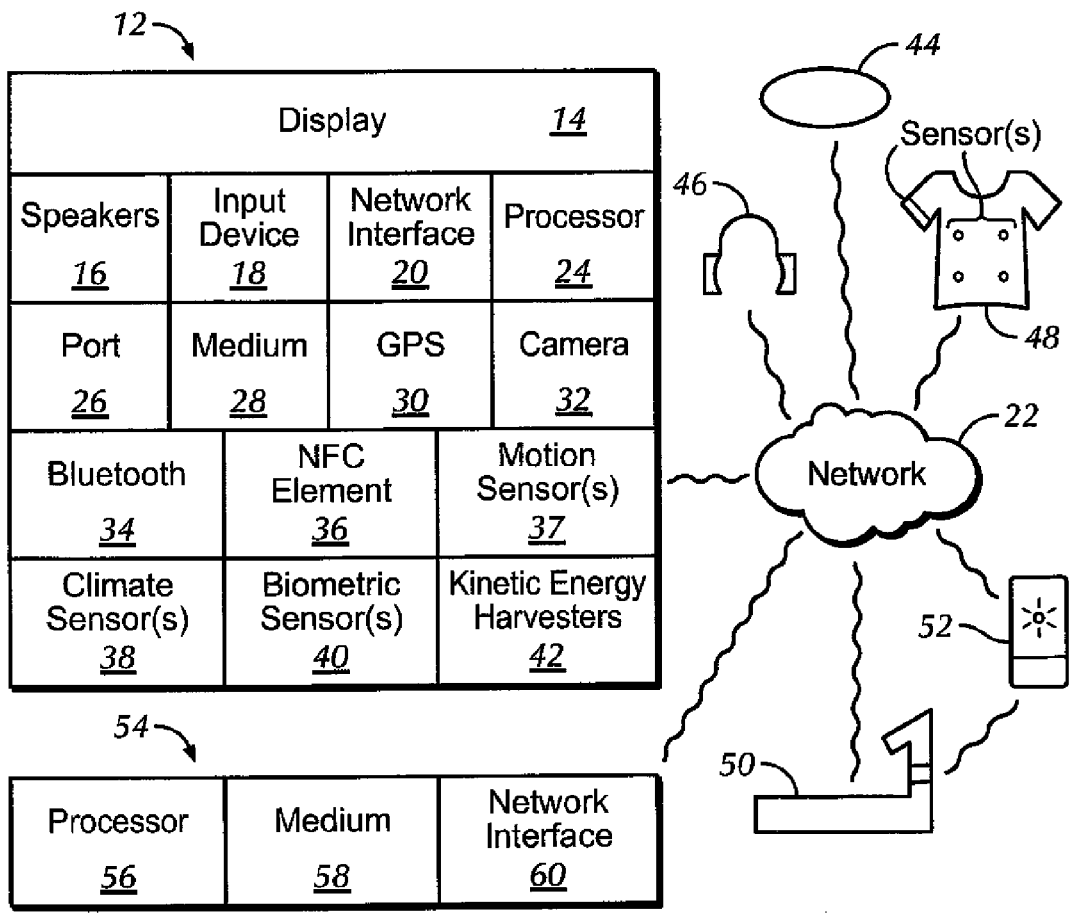
FIG. 1 is a block diagram of an example system including an example CE device in accordance with present principles.

This disclosure relates generally to consumer electronics (CE) device based user information. With respect to any computer systems discussed herein, a system herein may include server and client components, connected over a network such that data may be exchanged between the client and server components. The client components may include one or more computing devices including portable televisions (e.g. smart TVs, Internet-enabled TVs), portable computers such as laptops and tablet computers, and other mobile devices including smart phones and additional examples discussed below. These client devices may employ, as non-limiting examples, operating systems from Apple, Google, or Microsoft. A Unix operating system may be used. These operating systems can execute one or more browsers such as a browser made by Microsoft or Google or Mozilla or other browser program that can access web applications hosted by the Internet servers over a network such as the Internet, a local intranet, or a virtual private network.

As used herein, instructions refer to computer-implemented steps for processing information in the system. Instructions can be implemented in software, firmware or hardware; hence, illustrative components, blocks, modules, circuits, and steps are set forth in terms of their functionality.

A processor may be any conventional general purpose single- or multi-chip processor that can execute logic by means of various lines such as address lines, data lines, and control lines and registers and shift registers. Moreover, any logical blocks, modules, and circuits described herein can be implemented or performed, in addition to a general purpose processor, in or by a digital signal processor (DSP), a field programmable gate array (FPGA) or other programmable logic device such as an application specific integrated circuit (ASIC), discrete gate or transistor logic, discrete hardware components, or any combination thereof designed to perform the functions described herein. A processor can be implemented by a controller or state machine or a combination of computing devices.

Any software modules described by way of flow charts and/or user interfaces herein can include various sub-routines, procedures, etc. It is to be understood that logic divulged as being executed by a module can be redistributed to other software modules and/or combined together in a single module and/or made available in a shareable library.

Logic when implemented in software, can be written in an appropriate language such as but not limited to C# or C++, and can be stored on or transmitted through a computer-readable storage medium such as a random access memory (RAM), read-only memory (ROM), electrically erasable programmable read-only memory (EEPROM), compact disk read-only memory (CD-ROM) or other optical disk storage such as digital versatile disc (DVD), magnetic disk storage or other magnetic storage devices including removable thumb drives, etc. A connection may establish a computer-readable medium. Such connections can include, as examples, hard-wired cables including fiber optics and coaxial wires and digital subscriber line (DSL) and twisted pair wires. Such connections may include wireless communication connections including infrared and radio.

In an example, a processor can access information over its input lines from data storage, such as the computer readable storage medium, and/or the processor accesses information wirelessly from an Internet server by activating a wireless transceiver to send and receive data. Data typically is converted from analog signals to digital and then to binary by circuitry between the antenna and the registers of the processor when being received and from binary to digital to analog when being transmitted. The processor then processes the data through its shift registers to output calculated data on output lines, for presentation of the calculated data on the CE device.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

Before describing FIG. 1, it is to be understood that the CE devices and software described herein are understood to be usable in the context of a digital ecosystem. Thus, as understood herein, a computer ecosystem, or digital ecosystem, may be an adaptive and distributed socio-technical system that is characterized by its sustainability, self-organization, and scalability. Inspired by environmental ecosystems, which consist of biotic and abiotic components that interact through nutrient cycles and energy flows, complete computer ecosystems consist of hardware, software, and services that in some cases may be provided by one company, such as Sony Electronics. The goal of each computer ecosystem is to provide consumers with everything that may be desired, at least in part services and/or software that may be exchanged via the Internet. Moreover, interconnectedness and sharing among elements of an ecosystem, such as applications within a computing cloud, provides consumers with increased capability to organize and access data and presents itself as the future characteristic of efficient integrative ecosystems.

Two general types of computer ecosystems exist: vertical and horizontal computer ecosystems. In the vertical approach, virtually all aspects of the ecosystem are associated with the same company (e.g. produced by the same manufacturer), and are specifically designed to seamlessly interact with one another. Horizontal ecosystems, one the other hand, integrate aspects such as hardware and software that are created by differing entities into one unified ecosystem. The horizontal approach allows for greater variety of input from consumers and manufactures, increasing the capacity for novel innovations and adaptations to changing demands. But regardless, it is to be understood that some digital ecosystems, including those referenced herein, may embody characteristics of both the horizontal and vertical ecosystems described above.

Accordingly, it is to be further understood that these ecosystems may be used while engaged in physical activity to e.g. provide inspiration, goal fulfillment and/or achievement, automated coaching/training, health and exercise analysis, convenient access to data, group sharing (e.g. of fitness data), and increased accuracy of health monitoring, all while doing so in a stylish and entertaining manner. Further still, the devices disclosed herein are understood to be capable of making diagnostic determinations based on data from various sensors (such as those described below in reference to FIG. 1) for use while exercising, for exercise monitoring (e.g. in real time), and/or for sharing of data with friends (e.g. using a social networking service) even when not all people have the same types and combinations of sensors on their respective CE devices.

Thus, it is to be understood that the CE devices described herein may allow for easy and simplified user interaction with the device so as to not be unduly bothersome or encumbering e.g. before, during, and after an exercise.

In an example, the CE device processor can access information over its input lines from data storage, such as the computer readable storage medium, and/or the processor accesses information wirelessly from an Internet server by activating a wireless transceiver to send and receive data. Data typically is converted from analog signals to digital and then to binary by circuitry between the antenna and the registers of the processor when being received and from binary to digital to analog when being transmitted. The processor then processes the data through its shift registers according to algorithms to output calculated data on output lines, for presentation of the calculated data on the CE device.

An example algorithm that can be employed according to present principles is D=RT, where D) equals distance of a route. R equals speed (when D is a scalar) or velocity (when D is a vector) of the user in traversing the route, and T is the time it takes for the user to traverse the route at rate R. Two of the three variables are known or assumed and the third is solved for. For example, D typically is known either by receiving a route from the user and then looking up the distance of the route using electronically stored map information. Or, D is known from a user inputting a desire to traverse a route of a user-defined length. R can be known by accessing a user's past history of pace, or by using a default pace of the average user, or by receiving a user input of a desired pace including a qualitative input ("fast" or slow" e.g.) and then correlating the qualitative input to a quantitative pace using heuristic rules. T may be known by receiving a user-desired exercise time period. Or, T may be known by accessing the user's electronically-stored calendar schedule to determine when the user's next appointment is, where it is, determining a travel time to the location of the appointment from the user's present location based on map and traffic data that may be received over the Internet, and then adding a heuristically established "clean up" period to the travel time to allow the user to appropriately prepare himself for the appointment after exercising. The travel time and "clean up" period can be deducted from the appointment time to produce an "end of exercise" time, i.e., the time the user's exercise must end. The period between commencement of exercise and the "end of exercise" time can he set to equal T.

Accordingly, the CE device processor can access calendar information including scheduled events of a user, either from local storage or from the cloud. Likewise, map information can be accessed from local storage or the cloud, and location information indicating current location of the user can be obtained from the position sensor such as a GPS receiver on the CE device. This information can be stored at least temporarily in memory associated with the processor.

On an input line from one of the input devices described above, the processor can receive user input indicating a desire for route information, Based on time constraints indicated from the calendar information, the processor accesses the location information and map information to determine a route that is audibly and/or visually displayed on the device by outputting route information on an output line or lines of the processor (through appropriate conversion circuitry) to the sneakers and display, respectively.

As an example, suppose the user inputs a command to "give me a route I can run at my usual pace and still be at my next appointment on time". In one example, the processor determines the "end of exercise" time as described above (with or without the "clean up" period) and then determines T (exercise period) as the time period between the current time and the end of exercise time. The processor then accesses local or cloud storage to obtain the user's usual pace (R), or lacking a value, the processor can assume an ordinary exerciser's pace based on heuristics that may be keyed to age, e.g., if the user is between 20 and 30 years old, a pace of 7 minutes per mile may be used, if the user is between 30 and 40 years of age, a pace of 8 minutes per mile may be used, etc. The user's age may have been previously provided by the user and stored in the CE device, or it may be assumed to a default age if no value exists, or the processor may automatically access the Internet to perform a search for the user on, e.g., social network sites or other sites to lookup the user's age. The age in such a case is downloaded through the wireless transceiver and stored in local memory associated with the processor.

With T and R thus known, the processor then determines a route distance using the algorithm above. The processor then accesses the map information to iteratively build a route, preferably a dosed circuit so that the user ends the run where he started. The processor can build a route by calculating a distance from the user's current location to the next block at which a first right turn onto a cross street is possible, calculate the distance from that turn to the next right turn, then calculate the distance from that turn to a third right turn. The distance from this final turn to the origin is calculated and the four legs added together, with the sum being compared to the calculated distance D. If the sum equals D to within a threshold, e.g., if the sum equals D+−10% of D(D plus or minus ten percent of D), the calculated route is output for display.

If the sum does not equal D, the processor calculates a new route iteratively. For example, the next iteration of calculation can include calculating a distance from the user's current location to the second block (after the first block) at which a right turn onto a cross street is possible, calculate the distance from that turn to the next right turn, then calculate the distance from that turn to a third right turn that in this iteration typically with be the second right turn possible on that third leg, to match the length of the first leg. The distance from this final turn to the origin is calculated and the four legs added together, with the sum being compared to the calculated distance D. If sum equals D to within a threshold, e.g., if the sum equals D+−10% of D) (D plus or minus ten percent of D), the calculated route is output for display, Otherwise, a new route is determined, either by extending the initial (and third) legs by another block, or by extending the second (and fourth) legs by another leg.

While the above example is but one way to determine a route given a demanded or calculated distance, it is to be understood that other techniques may be used.

In addition, the processor may access route information provided by users other than the user of the device, with the route information indicating popular routes. This "popular" route information can he used to determine a route. For example, popular route information may be accessed by the processor through the wireless transceiver from social networking sites On the Internet and downloaded and stored on local storage. The processor can calculate the distance of the nearest popular route from the current user location, add it to the distance of the popular route itself as determined by the processor, e.g., using the map information and compare the sum to D. If the sum equals D) with threshold accounted for, e.g., if the sum equals D+−10% of D (D plus or minus ten percent of D), the popular route (and the initial route to net to the popular route) is output for display. If the sum is greater than D) within the threshold, the processor can iteratively decrease the popular route using principles described above until the sum equals D) within the threshold. If the sum is less than D with threshold accounted for, the processor can iteratively increase the popular route using principles described above until the sum equals D within the threshold.

Similarly, past route information indicating routes previously taken by the user of the device can be accessed (e.g., from the cloud or from focal storage) by the processor and used to determine a route. The processor can calculate the distance of the nearest past route from the current user location, add it to the distance of the past route itself as determined by the processor, e.g., using the map information and compare the sum to D. If the sum equals D with threshold accounted for, e.g., if the sum equals D+−10% of D (D plus or minus ten percent of D), the past route (and the initial route to get to the past route) is output for display. If the sum is greater than D within the threshold, the processor can iteratively decrease the past route using principles described above until the sum equals D within the threshold. If the sum is less than D with threshold accounted for, the processor can iteratively increase the past route using principles described above until the sum equals D within the threshold.

In outputting a route, the processor may output both directions along the way to remain on route, and time left to traverse the route based on R or based on an updated actual user pace as calculated by the processor using differences in current location information every, e.g., 30 seconds. The processor may also output social network information regarding the route on a display of the device. For example, the processor accessing the social network information may note that another social network user has used a keyword (e.g., of a street or trail name) that the processor correlates to the route using the map information. The processor may output the N words before and after the keyword in the social network message, for example, the processor may output "Jim says that a tree has fallen across the trail a half mile ahead", with the processor determining the half mile output using map information and a stated location of the tree from the social network site. The processor may then automatically calculate a detour to avoid the location and ask the user if he wishes to know an alternate route to detour around the reported obstacle. Thus, it is to be understood that the systems and devices described herein are able to present CE device users with comparative information about an initial and/or primary route, and also one or more alternative routes. The user may also be provided (e.g. on a UI) with a comparison of total distances of the primary and alternate routes, comparisons of estimated time to completion, comparisons of difficulties of the routes, and estimated calories/energy to be expended on the various routes.

Now specifically referring to FIG. 1, an example system 10 is shown, which may include one or more of the example devices mentioned above and described further below to enhance fitness experiences in accordance with present principles. The first of the example devices included in the system 10 is an example consumer electronics (CE) device 12 that may be waterproof (e.g., for use while swimming). The CE device 12 may be, e.g., a computerized Internet enabled ("smart") telephone, a tablet computer, a notebook computer, a wearable computerized device such as e.g. computerized Internet-enabled watch, a computerized Internet-enabled bracelet, other computerized Internet-enabled fitness devices, a computerized Internet-enabled music player, computerized Internet-enabled head phones, a computerized Internet-enabled implantable device such as an implantable skin device, etc., and even e.g. a computerized Internet-enabled television (TV). Regardless, it is to be understood that the CE device 12 is configured to undertake present principles (e.g. communicate with other CE devices to undertake present principles, execute the logic described herein, and perform any other functions and/or operations described herein).

Accordingly, to undertake such principles the CE device 12 can include some or all of the components shown in FIG. 1. For example, the CE device 12 can include one or more touch-enabled displays 14, one or more speakers 16 for outputting audio in accordance with present principles, and at least one additional input device 18 such as e.g. an audio receiver/microphone for e.g. entering audible commands to the CE device 12 to control the CE device 12. The example CE device 12 may also include one or more network interfaces 20 for communication over at least one network 22 such as the Internet, an WAN, an LAN, etc. under control of one or more processors 24. It is to be understood that the processor 24 controls the CE device 12 to undertake present principles, including the other elements of the CE device 12 described herein such as e.g. controlling the display 14 to present images thereon and receiving input therefrom. Furthermore, note the network interface 20 may be, e.g., a wired or wireless modem or router, or other appropriate interface such as, e.g., a wireless telephony transceiver, WiFi transceiver, etc.

In addition to the foregoing, the CE device 12 may also include one or more input ports 26 such as, e.g., a USB port to physically connect (e.g. using a wired connection) to another CE device and/or a headphone port to connect headphones to the CE device 12 for presentation of audio from the CE device 12 to a user through the headphones. The CE device 12 may further include one or more tangible computer readable storage medium 28 such as disk-based or solid state storage, it being understood that the computer readable storage medium 28 may not be a carrier wave. Also in some embodiments, the CE device 12 can include a position or location receiver such as but not limited to a GPS receiver and/or altimeter 30 that is configured to e.g. receive geographic position information from at least one satellite and provide the information to the processor 24 and/or determine an altitude at which the CE device 12 is disposed in conjunction with the processor 24. However, it is to be understood that that another suitable position receiver other than a GPS receiver and/or altimeter may be used in accordance with present principles to e.g. determine the location of the CE device 12 in e.g. all three dimensions.

Continuing the description of the CE device 12, in some embodiments the CE device 12 may include one or more cameras 32 that may be, e.g., a thermal imaging camera, a digital camera such as a webcam, and/or a camera integrated into the CE device 12 and controllable by the processor 24 to gather pictures/images and/or video in accordance with present principles (e.g. to share aspects of a physical activity such as hiking with social networking friends). Also included on the CE device 12 may be a Bluetooth transceiver 34 and other Near Field Communication (NFC) element 36 for communication with other devices using Bluetooth and/or NFC technology, respectively. An example NFC element can be a radio frequency identification (RFID) element.

Further still, the CE device 12 may include one or more motion sensors 37 (e.g., an accelerometer, gyroscope, cyclometer, magnetic sensor, infrared (IR) motion sensors such as passive IR sensors, an optical sensor, a speed and/or cadence sensor, a gesture sensor (e.g. for sensing gesture command), etc.) providing input to the processor 24. The CE device 12 may include still other sensors such as e.g. one or more climate sensors 38 (e.g. barometers, humidity sensors, wind sensors, light sensors, temperature sensors, etc.) and/or one or more biometric sensors 40 (e.g. heart rate sensors and/or heart monitors, calorie counters, blood pressure sensors, perspiration sensors, odor and/or scent detectors, fingerprint sensors, facial recognition sensors, iris and/or retina detectors, DNA sensors, oxygen sensors (e.g. blood oxygen sensors and/or VO2 max sensors), glucose and/or blood sugar sensors, sleep sensors (e.g. a sleep tracker), pedometers and/or speed sensors, body temperature sensors, nutrient and metabolic rate sensors, voice sensors, lung input/output and other cardiovascular sensors, etc.) also providing input to the processor 24. In addition to the foregoing, it is noted that in some embodiments the CE device 12 may also include a kinetic energy harvester 42 to e.g. charge a battery (not shown) powering the CE device 12.

Still referring to FIG. 1, in addition to the CE device 12, the system 10 may include one or more other CE device types such as, but not limited to, a computerized Internet-enabled bracelet 44, computerized Internet-enabled headphones and/ or ear buds 46, computerized Internet-enabled clothing 48, a computerized Internet-enabled exercise machine 50 (e.g. a treadmill, exercise bike, elliptical machine, etc.), etc. Also shown is a computerized Internet-enabled gymnasium entry kiosk 52 permitting authorized entry to a gymnasium housing the exercise machine 50. It is to be understood that other CE devices included in the system 10 including those described in this paragraph may respectively include some or all of the various components described above in reference to the CE device 12 such but not limited to e.g. the biometric sensors and motion sensors described above, as well as the position receivers, cameras, input devices, and speakers also described above.

Thus, for instance, the headphones/ear buds 46 may include a heart rate sensor configured to sense a person's heart rate when a person is wearing the head phones, the clothing 48 may include sensors such as perspiration sensors, climate sensors, and heart sensors for measuring the intensity of a person's workout, the exercise machine 50 may include a camera mounted on a portion thereof for gathering facial images of a user so that the machine 50 may thereby determine whether a particular facial expression is indicative of a user struggling to keep the pace set by the exercise machine 50 and/or an NFC element to e.g. pair the machine 50 with the CE device 12 and hence access a database of preset workout routines, and the kiosk 52 may include an NFC element permitting entry to a person authenticated as being authorized for entry based on input received from a complimentary NFC element (such as e.g. the NFC element 36 on the device 12). Also note that all of the devices described in reference to FIG. 1, including a server 54 to be described shortly, may communicate with each other over the network 22 using a respective network interface included thereon, and may each also include a computer readable storage medium that may not be a carrier wave for storing logic and/or software code in accordance with present principles.

Now in reference to the afore-mentioned at least one server 54, it includes at least one processor 56, at least one tangible computer readable storage medium 58 that may not be a carrier wave such as disk-based or solid state storage (and may include temporary storage on an Internet server through which copies of a program of instruction passes), and at least one network interface 60 that, under control of the processor 56, allows for communication with the other CE devices of FIG. 1 over the network 22, and indeed may facilitate communication therebetween in accordance with present principles. Note that the network interface 60 may be, e.g., a wired or wireless modem or router, WiFi transceiver, or other appropriate interface such as, e.g., a wireless telephony transceiver.

Accordingly, in some embodiments the server 54 may be an Internet server, may facilitate fitness coordination and/or data exchange between CE device devices in accordance with present principles, and may include and perform "cloud" functions such that the CE devices of the system 10 may access a "cloud" environment via the server 54 in example embodiments to e.g. stream music to listen to while exercising and/or pair two or more devices (e.g. to "throw" music from one device to another).

Figure 2:
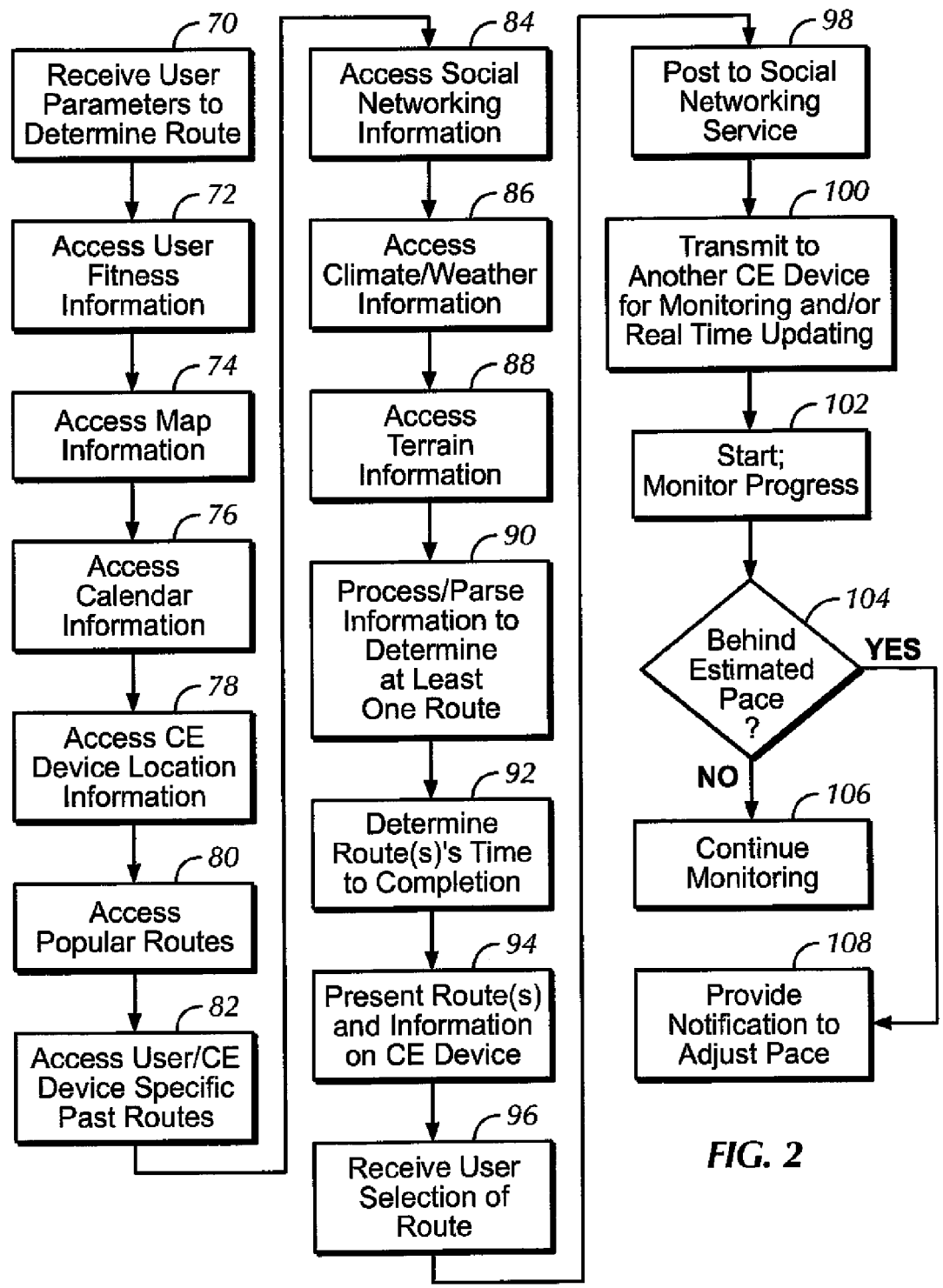
FIGS. 2 and 3 are example flowcharts of logic to be executed by a CE device to determine and/or alter routes in accordance with present principles.

Turning now to FIG. 2, an example flowchart of logic to be executed by a CE device such as the CE device 12 for determining a (e.g. exercise) route in accordance with present principles is shown. Beginning at block 70, the logic receives user input initiating route determination (e.g. software) and receiving various route parameters in accordance with present principles. It is to be understood that the user input received at block 70 may be a sequence of commands and/or user input including receiving one or more parameters (including any of those discussed herein) for which the route is to conform. Thus, for instance, the logic may receive user input of a desired total distance for the route, the desired start and end locations for the route, the maximum radius that any portion of the route may extend from e.g. the start location and/or a maximum time (e.g. at an estimated or average pace) it may take to get to a user-specified location regardless of the route, a route difficulty level, the desired type of terrain for the route, the desired net elevation gain or loss and/or total elevation gain or loss, etc.

Regardless, after block 70 the logic then moves to block 72 where the logic accesses fitness and/or biometric information associated with the user (e.g. by receiving/gathering input from biometric sensors in communication the CE device and measuring one or more types of biometric information associated with the user, based on user input of biometric information, etc.). The logic then proceeds to block 74 where map information is accessed such as from e.g. an online map service and/or from map information stored locally on the CE device. Note that the processor may determine e.g. based on the user input received at block 70 that only map information for a certain area need be accessed. For instance, based on user input instructing the CE device to create a route in the northern San Diego county area, the logic may access at least one online map service to acquire e.g. a topographical and/or road map of northern San Diego county only, and need not acquire all maps for every area in the world such as e.g. a United Kingdom road map or a topographical map of the Himalayan mountain range.

Regardless, after block 74 the logic proceeds to block 76 where the logic accesses the user's electronic calendar information to use as a route parameter (e.g., to determine if the user has any upcoming calendared events that may effect the time the user has to travel a route prior to the event(s) on the calendar and to thus generate a route that would allow the user enough time to complete the route yet still honor the user's appointments as denoted on the calendar). The logic may then continue to access various information in accordance with present principles for determining a route that best conforms to the user input received at block 70 and also is determined based on the information that is accessed as described below.

Thus, at block 78 current device location information is accessed (e.g. using a GPS receiver on the CE device), then at block 80 a database of popular routes is accessed (e.g., determined to be popular based on ratings of others and/or user reviews pertaining to route difficulty that was e.g. input by those other users using a fitness application configured for undertaking present principles), then at block 82 a database of past routes is accessed which the user of the CE device has traveled and even e.g. provided input to the CE device as a preferred route or acceptable future route, and then at block 84 social networking information pertaining to the user and/or user's friends is accessed (e.g. to determine if there is any location within proximity to the user that the logic correlates e.g. based on key words found in the user's social networking profile as being of interest to the user and hence determined by the processor as being a location which the route should pass by if possible while still accounting for the other information discussed herein). Still other information may be accessed for determining a route that conforms with as many parameters as possible, such as climate information like the current humidity and temperature at block 86, and other terrain information e.g. of the area around which the route will extend at block 88. Still other information may be accessed for the CE device to determine the route, such as e.g. traffic information, public service notifications of road closures, etc.

After accessing one or more pieces of information to be weighted when determining the route (e.g. and conformed with as much as possible), the logic then moves to block 90 where it analyzes and/or processes the map information and/or other information accessed and/or received at blocks 70-88 to determine one or more routes that conform to as much of the accessed information and/or parameters as possible. Thus, for instance, if the user indicated that a route was desired that was ten miles but that a margin of error of e.g. plus or minus one mile is acceptable as indicated by the user (e.g. manipulating a user interface to indicate that a route as little as nine miles but as much as eleven miles may be acceptable to the user), then the logic may analyze the map information to determine that a route beginning and ending where the user specified but that is nine and one half miles may take the user when traveling the route past a model plane demonstration area, where the logic correlated the model plane demonstration area from the map information with information in the user's social networking profile indicating that model planes are an interest of the user to thereby determine a route that would go past the demonstration area yet still conform at least to some of the other user-input parameters such as the start and end locations for the route.

After block 90 the logic proceeds to block 92 where the logic may calculate an estimated time to completion for each of the one or more routes determined at block 90. The estimated time to completion may be based on e.g. an average pace at which the user has traveled previous routes (e.g. including specifically an average pace of a previous route that included some of the same terrain and/or the same current climate conditions, and/or including adding average paces for various differing terrains to determine a total time to completion (e.g., the user goes twice as fast downhill as uphill) based on the length of each type of terrain divided by the average pace for that terrain) as e.g. tracked by the CE device using a position receiver. Note however that while the exemplary logic of FIG. 2 calculates an estimated time to completion at block 92 based on the routes determined at block 90, in some embodiments the user may have specified at e.g. block 70 a desired time to completion, which accordingly would have been processed at block 90 when determining the routes. Furthermore, a calculated estimated time to completion need not necessarily be exactly the same as e.g. a desired time to completion if one was input at block 70 if the user indicated a desired time to completion with a margin of error (e.g., the user wishes to embark on a fifteen minute run but indicates by manipulating a user interface that a route that would take plus or minus one additional minute than the fifteen is acceptable). Thus, it is to be understood that in some embodiments the user may specify a desired time to completion and the logic thus processes such information when determining one or more routes at block 90 while in other embodiments the user has not provided a desired time to completion.

Regardless, after block 92 the logic continues to block 94 where the logic presents the one or more routes on the CE device and may even present e.g. the estimated time to completion and total distance for each of the routes so that a user may select at least one of the routes as the one the user wishes to travel, selection of which is received by the logic at block 96. Once selected, the CE device may then instruct and/or aid the user at block 102 in traveling the selected route and monitoring the user's progress (and also e.g. biometrics) as discussed herein (e.g. the user selects "begin" and then the CE device instructs the user to proceed straight ahead, then turn right at a particular street, etc.).

However, note that the logic may also undertake other actions before block 102 such as e.g. publishing the selected route on a social networking service at block 98 so that the user's friends may see the route the user has selected, and even e.g. send the selected route directly to another one of the same user's CE devices at block 100 using e.g. NFC technology to thereby pair the other CE device with the one that determined the route(s) (e.g. tapping to sync the devices). Such "pairing" of devices may be suitable when e.g. a user uses a smart phone or laptop computer to create the route by inputting parameters such as start and end location, but then wishes that the route information be stored on headphones the user will actually be taking on the route so that the user need not take the laptop used to determine the route but still have the route information conveyed to the user while traveling. Accordingly, present principles recognize that the logic steps occurring at and after block 102 may be executed by the same or a different CE device that was "paired" at block 100.

In addition to or in lieu of the foregoing, at block 100 the selected route may also e.g. be transferred to another CE device for monitoring of the user by one of the user's associates as the user travels the route. For instance, a track coach may not actually embark on an exercise route with the user but may wish to track the user's progress and even monitor the user's biometric information in real time or at least substantially in real time, and accordingly the track coach's CE device may receive the route information e.g. over a WiFi connection.

In any case, after block 100 the logic moves to block 102 where e.g. the logic receives a start command to begin instructing the user on how to proceed geographically to follow the route and also monitor the user's progress. Thereafter, the logic may proceed to decision diamond 104 where the logic may (e.g. periodically such as at preset intervals and/or after expiration of a threshold time determined by the user and/or even the user's track coach) determine based on current position information whether the user while traveling the route is nonetheless behind an estimated pace and/or pace determined by the CE device as the minimum pace at which the route should be traveled so that a user may complete the route in time to e.g. still attend another event on the user's calendar. If the logic determines at block 104 that the user is not behind the estimated pace, the logic proceeds to block 106 where the logic continues monitoring the CE device's progress along the route, and thereafter may revert to diamond 104 at a later time to again determine if the user is behind the estimated pace. If however the logic determines at block 104 that the user is behind the estimated pace, the logic proceeds to block 108 where the logic provides a notification to the user that the user is behind pace and/or must begin traveling the route faster to complete the route e.g. before the user's upcoming meeting.

Figure 3:
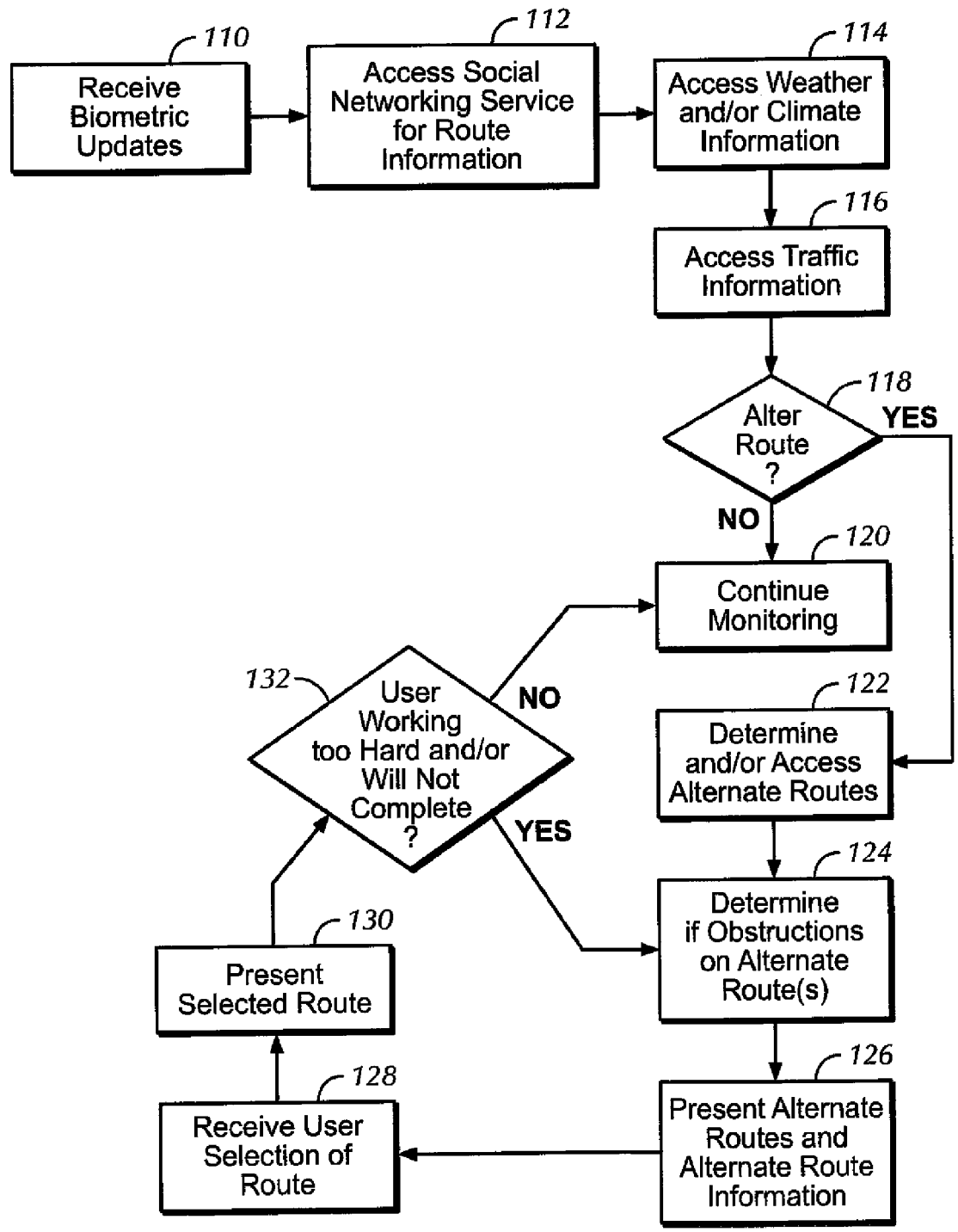

Continuing the detailed description in reference to FIG. 3, an example flowchart of logic to be executed by a CE device such as the CE device 12 for altering a route e.g. once the user has begun traveling the route is shown. Beginning at block 110, the logic receives real time biometric updates from one or more biometric sensors in communication with the CE device. Then at block 112 the logic accesses social networking information and determines if e.g. any of the social networking information pertains to the route based on e.g. key word correlations. Thus, for example, if the user's friend tweeted that there is traffic on Ted Williams Parkway in northern San Diego county, and the route at least partially includes traveling on Ted Williams Parkway, such a correlation may be made by the logic. Regardless, after block 112 the logic proceeds to block 114 where the logic accesses weather and/or climate information (e.g., current and/or future/predicted weather information) and then at block 116 accesses traffic information and even e.g. road construction information (e.g. by parsing text on a government website and making correlations as discussed herein). Accordingly, traffic/status information may be accessed at e.g. a signal alert website, a database containing crowd sourced information, and/or a government or private service maintaining a trail which is included on the route, for instance, and information therefrom may be compared and/or correlated to the route information to determine if traffic currently exists anywhere along the route.

Thus, at decision diamond 118 the logic determines whether the route being traveled should be altered. For instance, it may he determined at diamond 118 whether the route has any current obstructions thereon or other factors that may effect the user's ability to follow and/or complete the route. E.g., if based on the user's biometric information the logic determines that the user's body temperature is rising beyond an optimal and/or healthy level (e.g. which may have been preset by the user and/or the user's physician as a parameter) and also that the surrounding climate temperature is rising, the logic may dynamically determine that the upcoming bill on the route may no longer be optimal andfor possible for the user to travel under the current conditions. As another example, if a traffic jam has occurred alone the route, this may prevent the user from completing the route before an upcoming appointment on the user's calendar. In any case, if the logic determines that the route need not be altered at diamond 118, the logic proceeds to block 120 where the logic continues monitoring the route for obstructions, biometric information, the position of the CE. device, etc., and then may revert back to diamond 118 to make a subsequent determination regarding whether to alter the route at a later time.

If, however the logic determines at diamond 118 that the route should be altered, the logic instead proceeds to block 122 where the logic determines and/or accesses alternate routes. For example, if the CE device at that time is able to connect to a network such as the Internet, another route may be determined from the current position of the CE device back to the ending location while taking account for other real-time information that may affect the user's ability to travel alternate routes such as any possible traffic jams thereon, even if such an alternate route does not comply with all the parameters input by the user (e.g. if the user wished to travel up a hill but based on the user's biometrics and the current climate that traveling up the hill is no longer optimal). However, present principles recognize that an alternate route should nonetheless comply with as many parameters as possible so that e.g. the user-input total distance that the user input is used when determining an alternate route so that e.g. the user still travels the distance but avoids traffic, the hill, etc. Also note that e.g. if one or more routes and/or map information is stored on the CE device itself and/or if the CE device at that time is unable to connect to a network, such locally stored information may be used to nonetheless still determine an alternate route or detour.

Still in reference to FIG. 3, after block 122 the logic proceeds to block 124 where the logic may gather and analyze current information on the one or more alternate routes to determine if any obstructions or other factors are present on the alternate route that would also not be optimal and/or in conformance with one or more of the parameters discussed herein. If such a condition(s) exists, at block 126 the logic notifies the user of the one or more alternate routes and also notifies the user of any obstructions and/or that the alternate route is available but does not conform to one or more of the user-input parameters for the initial route. Then at block 128 the logic receives user input selecting one of the alternate routes and/or selecting to continue on the current route, and then the logic proceeds to block 130 where the logic presents the selected route accordingly.

Thereafter, the logic proceeds to decision diamond 132 where the logic may determine (e.g. based on biometric information in accordance with present principles) whether the user is over-exerting himself or herself e.g. on the alternate route by e.g. comparing the biometric information to a table of optimal biometric levels for the particular biometric information and/or user-specific optimal biometric levels. For instance, the logic may determine at diamond 132 whether a current heart rate for the user is within a heart rate range that is not user specific but that is accepted as being within a healthy range for a heart rate while engaged in physical activity based on a table of acceptable and unacceptable heart rate ranges, and/or may determine whether the user's current heart rate exceeds a doctor-prescribed heart rate for the user stored as data on the CE device or otherwise accessible to the CE device. Also at diamond 132 the logic may determine based on the current position of the CE device with the person whether the user will complete the route in the estimated time. If one or more of the determinations made at diamond 132 is made in the negative, the logic may revert back to block 120 and proceed from there. If however one or more of the determinations made at diamond 132 is made in the affirmative, the logic may instead revert to block 122 and may continue from there.

Figure 4:
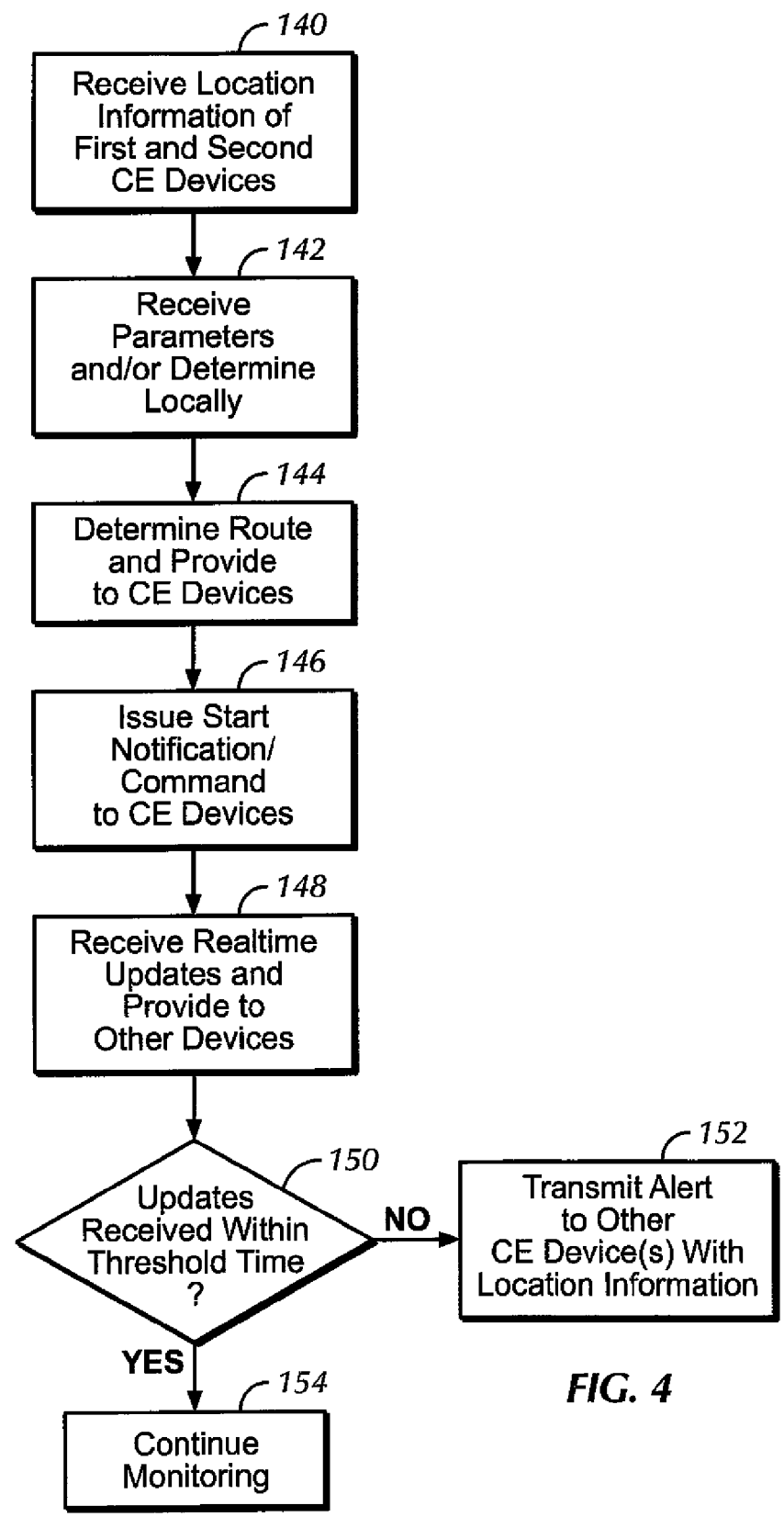
FIG. 4 is an example flowchart of logic to be executed by a server in accordance with present principles.

Before moving on to FIG. 4, it is to be understood that e.g. if the user's biometric information is beyond an acceptable range as described above, in some embodiments the logic rather than providing alternate routes may instruct the user to stop moving and/or following any route. The logic may also present a prompt e.g. requesting whether the CE device should automatically contact an emergency service and provide location information for the user, and/or may automatically do so without user input if e.g. the biometric information is outside of a threshold for which medical attention would otherwise not be necessary. Thus, for instance, if the logic were to detect a heart attack, the logic may automatically without user input notify an emergency service over a network and transmit location information of the CE device and hence the user to the emergency service so that the emergency service may locate the user and provide him or her with medical attention.

Now in reference to FIG. 4, an example flowchart of logic to be executed by a server in communication with one or more CE devices for e.g. determining a route at a server in accordance with present principles is shown. Beginning at block 140, the logic receives location information of first and second CE devices, and then at block 142 the logic receives route parameters from the CE devices (e.g. as input by the users of the CE devices), and/or may determine route parameters at the server as well. In any case, at block 144 the server then determines a route and provides the route to the CE devices. Thereafter, at block 146 the logic issues a start notification to the CE devices to e.g. instruct the CE devices to present a notification that the users should begin traveling the route. Also at block 146 the logic may begin tracking the CE devices based on respective position information received therefrom.

The logic then proceeds to block 148 where the logic receives real-time position updates, and may even provide such position information to still other CE devices other than those of the users traveling the route. Using the track coach example again, the track coach may track the progress of one or more athletes as the server provides real-time position information from the athletes' CE devices to the coach's CE device. This also provides a safety feature so that the coach (e.g. and even the coach's CE device) may be able to determine that an emergency exists if the CE device begins deviating from the route or stops at a point on the route and does not progress any further.

Regardless, after block 148 the logic proceeds to decision diamond 150 where the logic may determine whether a position update has been received from one or more of the CE devices within a threshold time. The threshold time may be determined based on e.g. user input of a desired threshold time such as from one of the athletes or the coach in the example above. If an negative determination is made at diamond 150, the logic proceeds to block 152 where the logic transmits a notification to e.g. an emergency service and/or another CE device other than the one for which the position information was not received within the threshold time. The notification may include an indication that position information has not been received for the threshold time, and may also include other information such as e.g. the last-received location information for the CE device, the last-received biometric information of the user of the CE device, etc. Concluding FIG. 4, if a positive determination is made at diamond 150, the logic instead proceeds to block 154 where the logic continues monitoring the CE devices and/or receiving information therefrom, and may then proceed back to diamond 150 for a subsequent determination in accordance with present principles.

Turning now to FIG. 5, an exemplary user interface 160 presentable on a CE device for inputting route parameters in accordance with present principles is shown. The UI 160 includes a distance field 162 for inputting a desired distance and even a range of distances, a total time field 164 for inputting a total time to completion for the route and even a time range rather than a specific time, a start location field 166 for inputting a start location for the route (note that a selector element 168 is also shown that is selectable to cause a representation of a map to be presented from which a user may select the start location by providing input to a particular portion of the map), and an end location field 170 for inputting an end location for the route (note that a selector element 172 is also shown that is selectable to cause a representation of a map to be presented from which a user may select the end location by providing input to a particular portion of the map). Also shown on the UI 160 is a maximum distance from start location field 174 for inputting a maximum radius from the start location that any portion of the route may extend in accordance with present principles, a difficulty level field 176 for inputting a general level of difficulty for a desired route that may be determined based on a number of factors and even a selector element 178 for selecting specific levels of difficulty as set forth below in reference to FIG. 6, a terrain field 180 for inputting one or more terrains that the route should include, and a fitness level field 182 for inputting a general level of fitness of the user that the CE device will process when determining a route (e.g. a person indicating they are "overweight" will cause the CE device to determine a route that is as flat as possible and avoids hills, and a person indicating that they are "fit" will cause the CE device to determine a route that based on the conditions would provide a strenuous exercise to e.g. strengthen the user's heart even further).

Before moving on to FIG. 6, also note that a selector element 181 for selecting a past route is shown that is selectable to cause a UI presenting previously traveled routes to be presented for selection, along with a selector element 183 for causing routes traveled (in the past, currently, or scheduled for the future) by friends to be presented on a UI on the CE device (e.g., based on information from a social networking service or a common software application) for selection. Last, note that a submit selector element 184 is shown for causing the CE device to determine one or more routes based on the parameters entered at the UI 160 in accordance with present principles. For completeness before moving on, also note that the fields described herein for user input may be manipulated e.g., by selecting the field using touch-screen manipulation and then manipulating e.g. a "soft" keyboard presented on the CE device to provide input.

Continuing now in reference to FIG. 6, an exemplary UI 186 is shown that may be e.g. automatically presented without further user input responsive to selection of the selector element 178 described above. The UI 186 includes one or more time fields 188 for a user to input an amount of time (e.g. five minutes) and one or more terrain fields 190 for the user to specify a type of terrain that the user wishes to travel for the amount of time indicated in the corresponding time field 188. Thus, for example, if the user indicates that the user wishes to travel on flat ground for five minutes, then go uphill for two minutes, and then downhill for five minutes, the CE device may analyze available map information to determine a route that best comports with those parameters based on e.g. the current pace of the user and/or estimated paces based on current weather conditions, past paces of the user for each of the differing terrains, etc. Last, note that a submit selector element 192 is shown for causing the CE device to determine one or more routes based on the parameters entered at the UI 160 and/or UI 186 in accordance with present principles.

Figure 7:
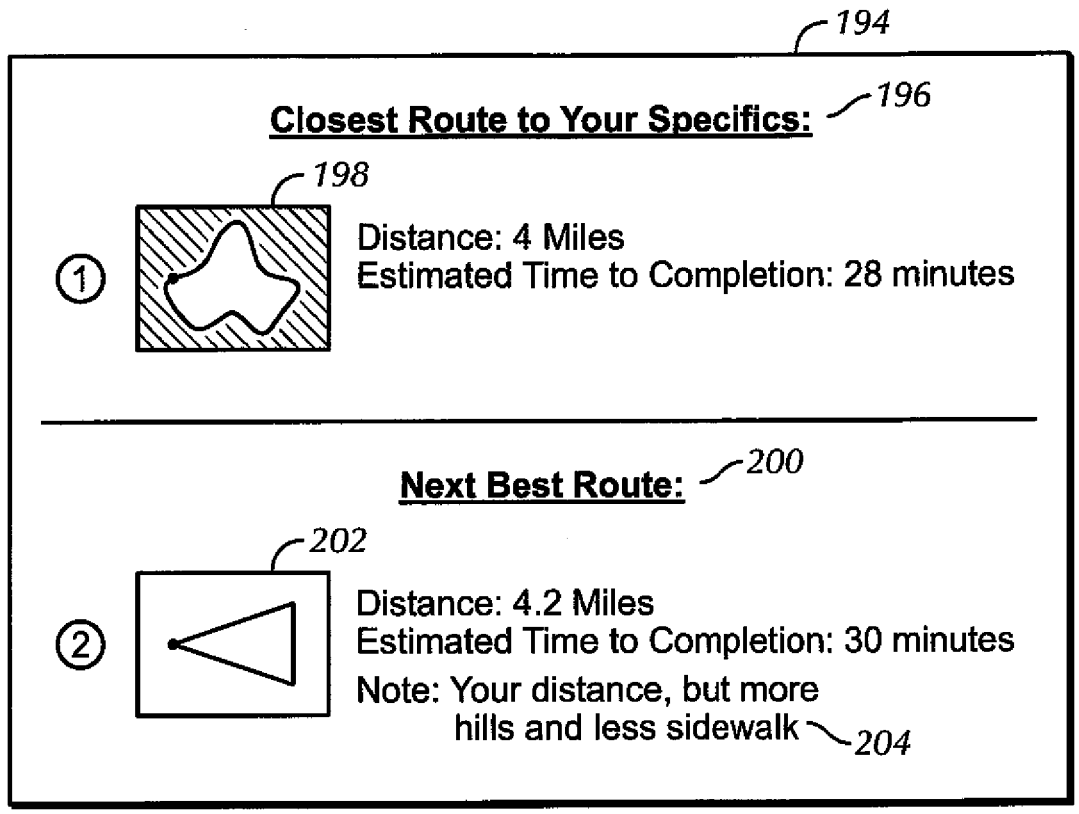

Now in reference to FIG. 7, a UI 194 is shown that may be presented on a CE device in accordance with present principles for selecting a route from one or more possible/available routes determined by the CE device in accordance with present principles. Thus, the UI 194 includes an indicator 196 indicating a route 198 represented as a thumbnail with an outline of the route on a map that most conforms to the parameters input by the user. Also included next to the route 198 and associated therewith is an indication 199 of information pertaining to the route such as e.g. the total distance of the route and/or the time to completion of the route. Also shown is an indicator 200 indicating a route 202 represented as a thumbnail with an outline of the route (e.g. overlaid) on a map that conforms to at least some of the parameters input by the user but not as many and/or not as closely as the route 198. Note that next to the route 202 is an indication 204 that contains information about the route in accordance with present principles (e.g. total distance, time to completion) and an indication e.g. of how the alternate route does or does not conform to one or more of the parameters. Note that in some embodiments, e.g. the thumbnail of the routes 198, 202 are selectable by a user to select the route as the one which the user desires to have presented on the CE device in accordance with present principles, and e.g. may even automatically cause the CE device to being issuing instructions on how to begin and/or follow the route.

Figure 8:
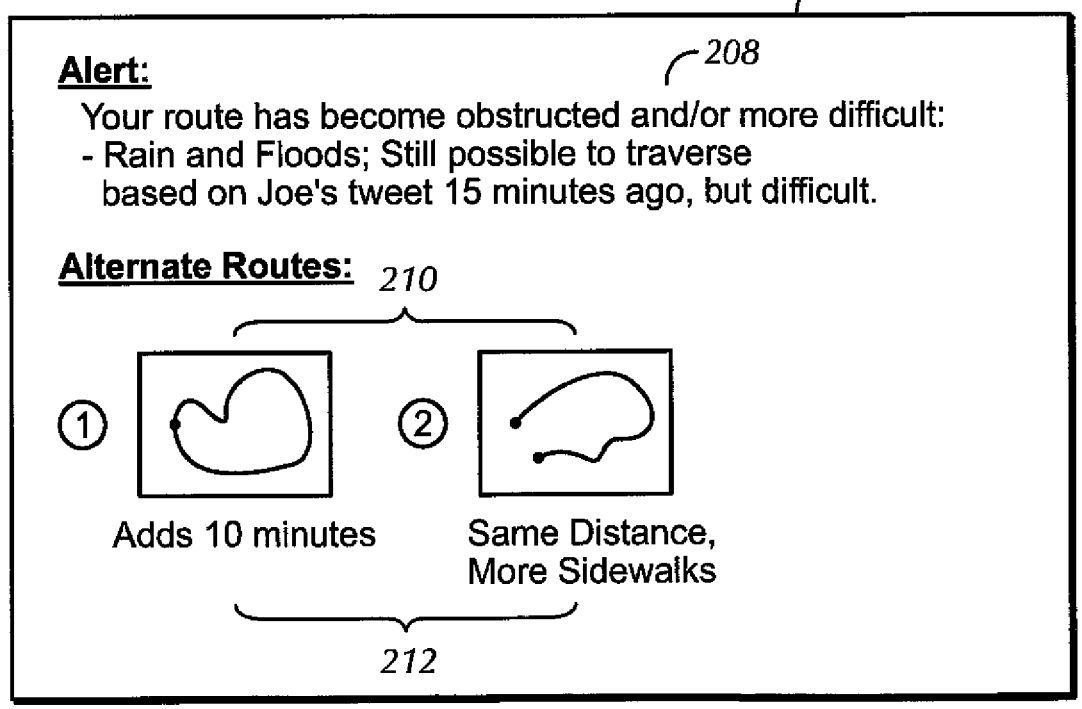

Turning now to FIG. 8, a user interface 206 is shown that is configured for providing information to a user once a CE device determines e.g. that an obstruction exists on the route and/or that the user will not be able to complete the route as initially estimated by the CE device (e.g. the user's pace slows as he or she progresses along the route). Thus, the UI 206 includes an indication 208 regarding such information, and in the present exemplary instance the indication 208 contains information informing the user that the route being traveled has become obstructed and/or more difficult (e.g. the surround climate temperature has increased, thereby requiring more physical effort to travel the route). The indication 208 may also contained detailed information about the obstruction such as e.g. that rain and/or floods have made passing a particular area of the route more difficult but also that based on other information such as a friend's social networking post the area is difficult but nonetheless still able to be traversed.

In addition to the foregoing, the UI 206 may also present at least one alternate route 210 determined by the CE device that is selectable by a user to cause the alternate route to be presented on the CE device and to cause the CE device to begin issuing instructions on how to follow the alternate route as opposed to the original route that has become obstructed. Also note that beneath each of the one or more alternate routes 210 are respective indications 212 of how the alternate route does or does not comport with parameters input by the user and/or how the alternate route differs from the route that has become obstructed. For instance, the indication 212 may indicate that the alternate route will take ten more minutes than the estimated time to completion of the obstructed route, and/or may indicate that the terrain is different than the terrain specified by the user.

Figure 9:
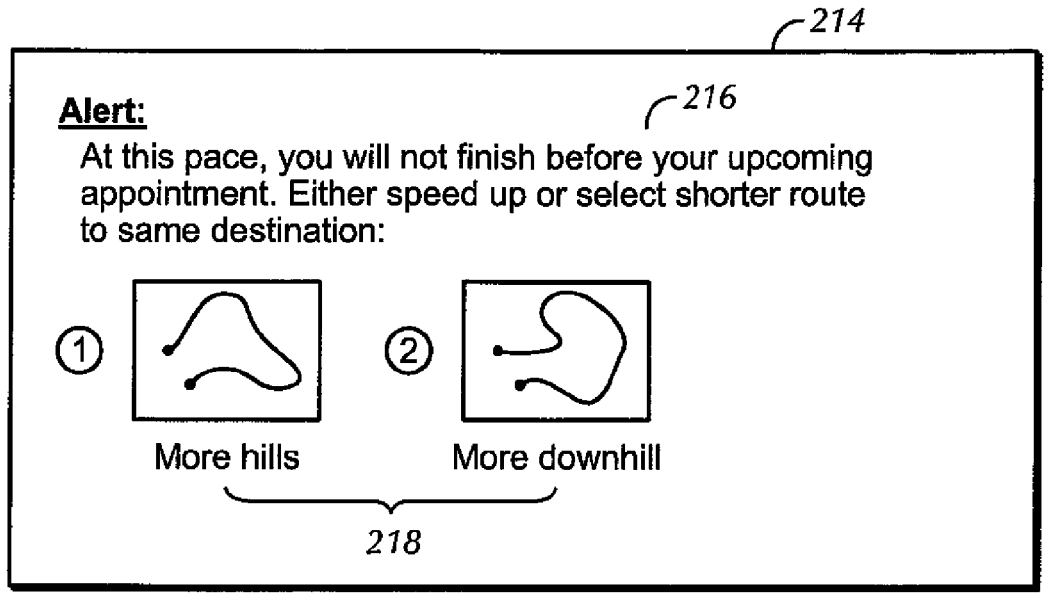

Continuing the detailed description in reference to FIG. 9, an exemplary UI 214 is shown that is presentable on a CE device in accordance with present principles to e.g. notify the user that the route being traveled will not be completed within an estimated time and/or before an upcoming calendar appointment. Thus, the UI 214 includes an indication 216 that, at the user's current pace, the user will not complete the route before an appointment on the user's calendar. The indication 216 also indicates that the user may undertake a faster pace in order to complete the route in time, and/or may select an alternate route(s) selector element 218 for alternate possible routes from the user's current location as determined by the CE device to arrive and an ending location previously input by the user, it being understood that the alternate route selector element 218 is selectable to cause the alternate route associated therewith to be presented on the CE device so that the user may travel the alternate route.

Figure 10:
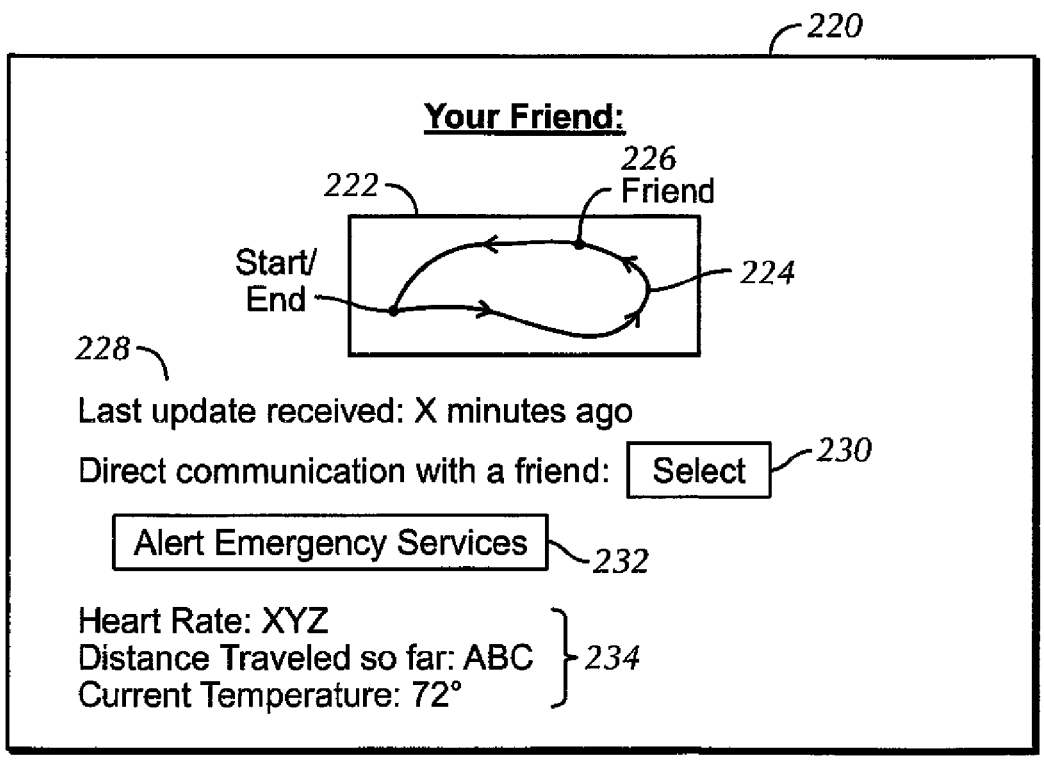

Now describing FIG. 10, an exemplary UI 220 is shown tor presenting current information of a route being traveled by some one else on a user's CE device (e.g. a track coach observing the progress of athletes, to borrow from the example above). The UI 220 thus shows a map 222 including an outline/tracing 224 of the route superimposed onto the map. The map 222 also includes an indication 226 (represented as a dot) denoting the (e.g. current and/or estimated) position of the person traveling the route. As may be appreciated from FIG. 10, beneath the map 222 on the UI 220 is an indication 228 of when the last update was received from the CE device of the person traveling the route and/or any of the other information pertaining to the route discussed herein, as well as a selector element 230 selectable to initiate a direct communication between the CE device presenting the UI 220 and the CE device of the person traveling the route (e.g. a telephone call, a text message, a "walkie talkie" direct communication, etc.).

The UI 220 also includes a selector element 232 selectable to initiate a function to contact an emergency service. Thus, for instance, if the CE device presenting the UI 220 receives information from the CE device of the person traveling the route that indicates the person traveling the route is having a medical emergency, that updates have not been received, that the user has deviated significantly from the route, etc., the selector element 232 may be selected cause the CE device to automatically contact an emergency service (e.g. automatically dial 911) and/or provide the most recently received location information to the emergency service. The UI may also include still other information 234 received from the CE device on the route, such as e.g. biometric information of the person traveling the route, the current distance traveled, the current temperature at or around the location of the person traveling the route, etc. Last before moving on to FIG. 11, note that the UI 220 may include information for more than one person traveling the same route or a different route such that a person may monitor a group of people using the UI 220.

Figure 11:
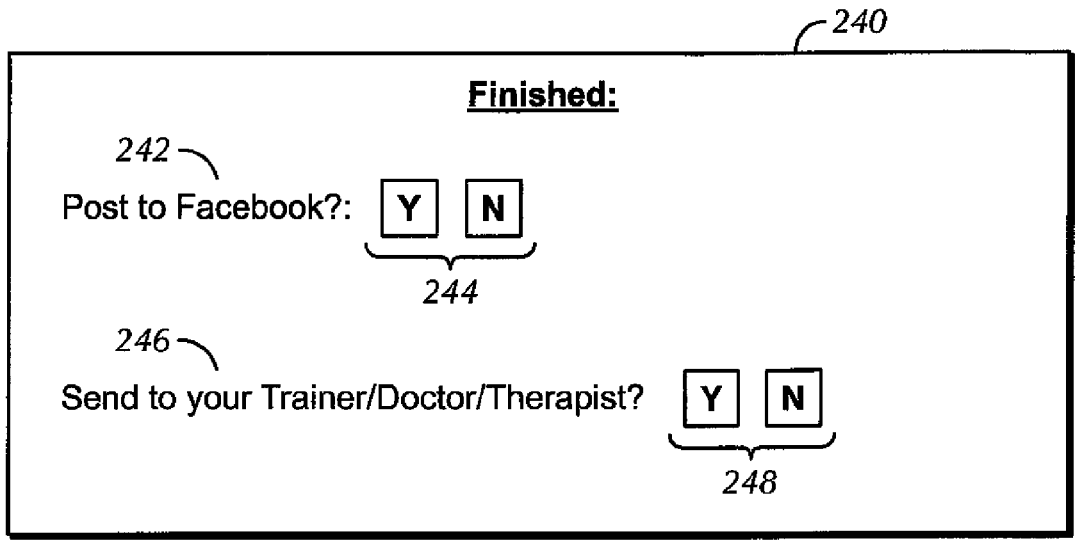

Now in reference to FIG. 11, an exemplary UI 240 is shown that may be presented on a CE device upon completion of a route in accordance with present principles. The UI 240 thus includes an option 242 requesting whether the user wishes to post the route and/or any information associated therewith (e.g. biometric information, distance traveled, time to completion, start and end locations, climate data, etc.) to one or more social networking site, and thus the UI 240 also includes yes and no selectors 244 for selecting whether to post the information or not. The UI 240 also includes an option 246 requesting whether the user wishes to provide one or more pieces of such information (e.g. biometric information, distance traveled, time to completion, start and end locations, climate data, etc.) to a trainer, medical professional, etc. over e.g. a network so that the medical professional can view the information to e.g. monitor the progress of a person's recovery and/or training.

Figure 12:
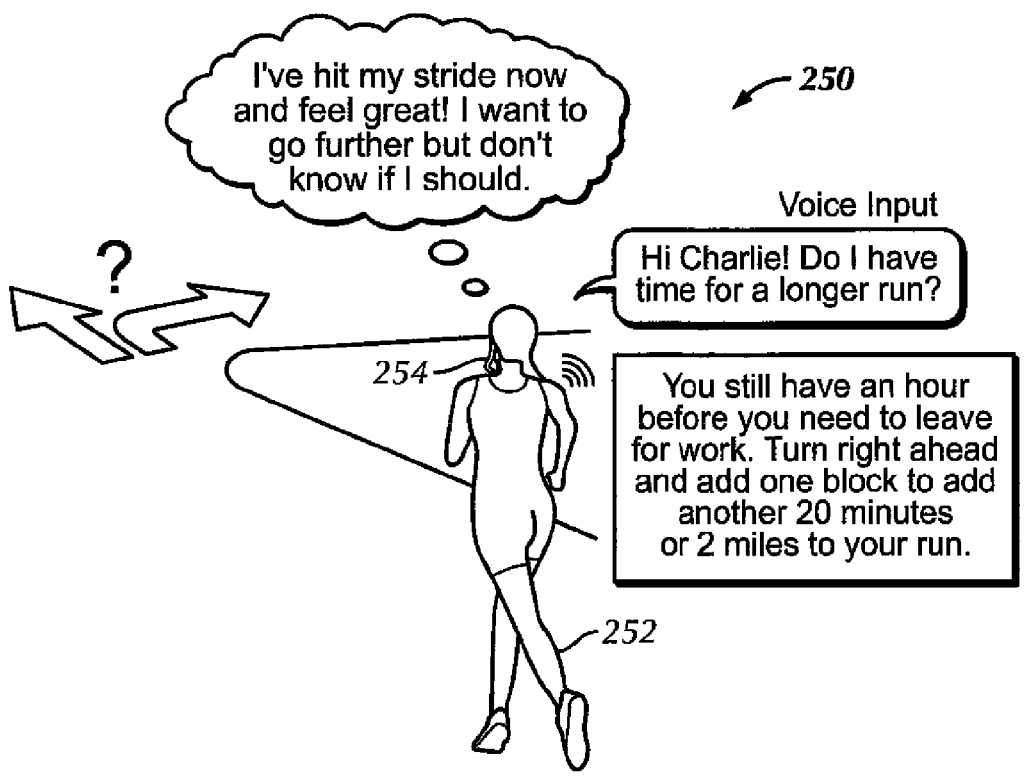
FIGS. 12 and 13 are illustrations that demonstrate present principles.

Continuing the detailed description in reference to FIG. 12, an illustration 250 is shown of a person 252 wearing a CE device 254 that in the exemplary instance are smart headphones. It may be appreciated from the captions in the illustration 250 that the person 252 provides audio input to the CE device 254 indicating that the user would like to travel further than the current distance of the route, and the CE device 254 thus audibly responds in turn (e.g. using a computerized voice) after modifying the route in accordance with present principles to suggest an alternate route along with information about the alternate route.

Figure 13:
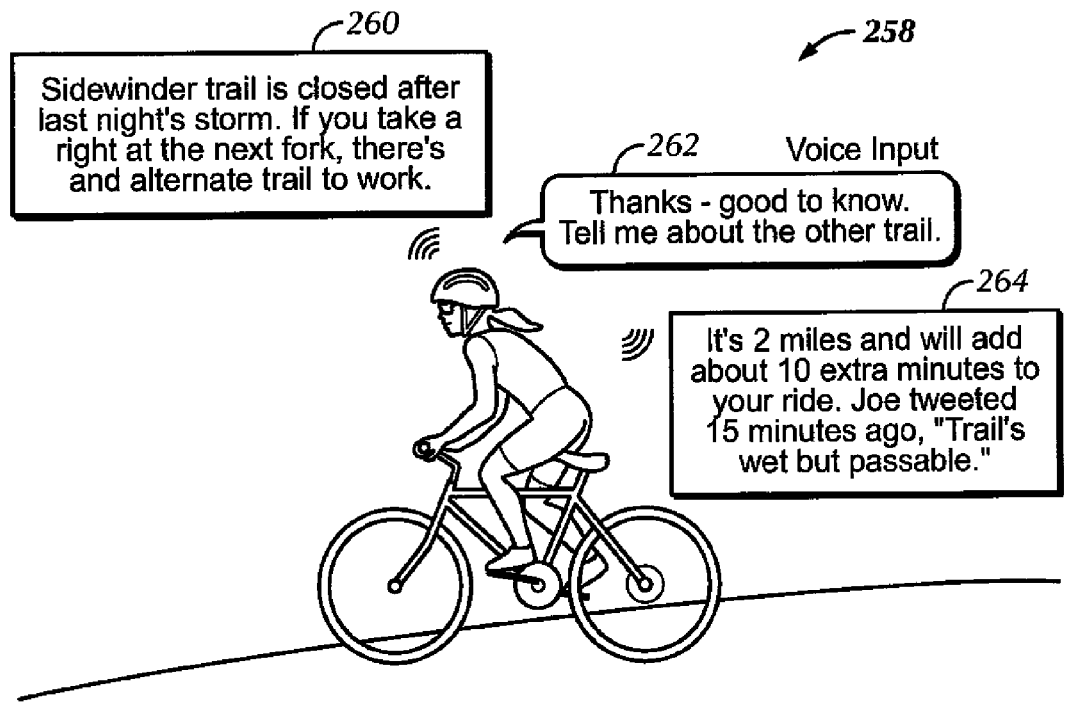

Another illustration 258 is shown in FIG. 13. As shown, caption 260 represents an audible notification from the CE device that there is an obstruction ahead on the route. Caption 262 represents audible input from the user requesting more information about an alternate route indicated in caption 260, and thus caption 264 provides the requested information, It may now be appreciated that e.g. route information in accordance with present principles may be based on previous workouts/routes, pre-set workouts, etc. The CE devices described herein may also act as a virtual trainer to provide input based on e.g. biometric data and estimated times to completion of a workout such as e.g. providing an estimate of the number of calories that would be burned by traveling a route and/or indicating that the user needs to go faster, keep going, etc. Also if desired, the user may specify e.g. using a UI that certain types of communications and/or other functions of the CE device should be blocked during the person's participation in a route, such as e.g. blocking text messaging notifications from being presented to the user until the route is complete.

Present principles also recognize that an exercise route may be "flagged," "tagged," or otherwise designated as being part of a person's physical therapy, and thus the CE device may access e.g. a website or database to determine prescribed therapy and thus create a route/exercise plan in conformance therewith, and also to communicate results back to e.g. a medical provider.

Present principles further recognize that factors/parameters to be used when determining an exercise route may include not just e.g. a desired distance or events on an electronic calendar, but also e.g. how the person slept the night before based on e.g. user input and/or sensors communicating with the CE device that monitored the person's sleep the night before. Present principles also recognize that the CE device may indicate to the user a particular pace at which a route should be traveled by e.g. presenting music that the user is to match to the user's cadence to thereby establish a pace, and that the user could even input a request for a different song with the same beat should the user not like the song initially presented by the CE device. Furthermore, in exemplary embodiments if the person wishes to pause the music to e.g. briefly stop traveling the route and to talk to some one that the user encountered, the user may provide a gesture command in free space to the CE device such as e.g. waving the person's hand in a certain (e.g. predefined) manner to thereby pause the music and/or instructions from the CE device on how to follow the route, though it is to be understood that e.g. removing an ear bud from the user's ear may pause the music if the ear bud has e.g. a heat or proximity sensor providing input to the CE device processor to thereby allow the CE device processor to determine that the ear bud is no longer in the person's ear and thus that the music should be paused. Also note that e.g. a gesture in free space command may be used to cause the CE device to present e.g. music with a faster beat for the user to match cadence therewith.

Also note that in exemplary embodiments e.g. the CE device may receive input of a desired distance in accordance with present principles, but may then e.g. determine a shorter or longer route than what was indicated by the desired distance that nonetheless would cause the user to exert the same physical effort/output. Thus, for instance, if the user indicated that he or she wished to run five miles on flat ground, but the surrounding terrain was full of hilly terrain, then the CE device may e.g. determine the user's fitness level based on one or more biometric pieces of information from the biometric sensors discussed above, and either shorten or extend the route based on an estimate of what the user's physical output would have been on flat ground to match that estimate when the hilly terrain is accounted for. Thus, for instance going downhill the user may have to travel further than he or she would on flat ground, and going uphill the user may have to travel shorter than he or she would on flat ground.

Also note that present principles may e.g. allow for interval training and/or tracking if a user e.g. is running around a quarter mile oval track. Such intervals may also be along a route determined by the CE device itself.

Present principles also recognize that the CE devices disclosed herein may dynamically change a user's planned route and/or workout if after a certain amount of time and/or based on the determinations discussed above, the CE device determines (e.g. based on one or more pieces of biometric information) that the route and/or time to completion is no longer obtainable, and can thus suggest alternatives accordingly. Furthermore, note that still other types of information may be used to determine a user's physical output, such as e.g. emotion recognition using images from a camera e.g. mounted on a bicycle being ridden that captures the user's face and may be analyzed by the CE device to e.g. determine if the user's skin is flushed, whether the user's temperature is rising too high too fast, is in distress or is struggling to keep pace, etc. Also note that such images may be analyzed by the CE devices disclosed herein to make determinations whether the user's posture, positioning, etc. for the given exercise is correct and notify the user if it is not.

Also note that the CE devices disclosed herein are understood to be capable of measuring a person's exertion based on a number of factors that are unique to that person for e.g. comparing to others also traveling the same route or that have previously traveled the route to determine what level of exertion the current user is to expect. Thus, for instance, different people perspire different amounts, hut based on other biometric information such as e.g. heart rate and cadence the user's exertion may be measured for comparison.

In reference to the types of terrain and routes for which user input may be received, a user may indicate e.g. that the user has a preference to run on sidewalks, dirt trails, past areas that include rest rooms/bath rooms, water supplies and/or fountains, to change elevation at specific number of e.g. feet up or down, to not travel into the wind, that a user does not wish to wait at traffic signals, does not wish to cross a highway, etc. and that the CE device based thereon will determine a route that as best as possible meets those criteria.

Furthermore, in some embodiments the UIs discussed herein may dynamically change over time so that e.g. if the CE device determines that a user more often than not selects routes with one or more common characteristics, the CE device may in the future use such common characteristics when determining routes to present to the user. Likewise, if a user does not often or at all select a route option having a certain characteristic, the CE device will no longer present routes that include that characteristic.

Referring back to the "alerts" described above and estimated checkpoints on the route that are estimates by the CE device for where a user is projected to be and when, should e.g. a user not reach the checkpoint of the route in the estimated time or at all (e.g. if the user's CE device temporarily is unable to communicate over a network such as "losing reception" and during that time the user sprains their ankle and can no longer continue), thereby failing to reach the "checkpoint," an alarm and/or notification may be provided to another CE device in accordance with present principles. In other words, it is to be understood that the CE devices described herein are configured to extrapolate where a person was when a last communication was received and where the user should be later, and e.g. a server may thus set an alarm automatically upon losing communication with the CE device for a future time based on an estimate of where the user should be in the future (e.g. even accounting for known areas on the route where mobile reception and/or network connectability is available). These alerts may be set based on e.g. one or more correlations using the data and/or information discussed herein, and indeed other CE devices in communication with the subject CE device may be able to present the same route and show where other CE devices on the route are currently located, and even e.g. compete with each other using the route, and even e.g. configure the CE device to instruct the person what can be done to surpass others also participating in the route (e.g., instructing the person that he or she must run one mile an hour faster in order to catch some one else).

Referring back to instances when e.g. a CE device is unable to connect to a network such as when it enters an area "without service," it is to be understood that information such as biometric information gathered by the CE device may be stored locally on the CE device until such time as the CE device is again able to e.g. communicate with a server to provide the information thereto. However, also note that in such instances, communication with two CE devices that each cannot connect to e.g. a wireless telephone network may nonetheless still create their own mobile "hot spot" to communicate with each other such as using e.g. NFC and/or Bluetooth technology. Also pertaining to instances where a CE device may not be able to connect to a network at a location during travel of the route, e.g., it is to be understood that the CE device may nonetheless present alternate routes based on the determinations discussed herein using e.g. one or more alternate routes and/or map information stored locally on the CE device e.g. that was stored thereon when the route was initially determined while the CE device was connected to a network.

Discussing the determinations above regarding whether an obstacle exists, such information may in fact be e.g. inferred by the CE device and need not necessarily e.g. access a traffic alert accident notification. For instance, if based on data received from other CE devices traveling the same route or at least a portion thereof, and/or based e.g. on social networking information pertaining to the route, if the CE device determines that the pace of other CE devices slows down in an area where no obstacles are known to exist, the CE device may infer that an obstacle does exist in the location and make determinations and/or present alternate routes accordingly.

Specifically discussing social networking aspects of present principles, as indicated above, a route which a user has or will be participating in may be shared over a social network. Then, e.g., a software application interfacing with the social network may be configured to e.g. allow a friend of the user to also cause the route or at least a portion thereof to be presented on the friend's CE device so that the friend may also travel the route and even meet up with the user, where the route for the friend may be e.g. adjusted based on the friend's different starting location but nonetheless encompassing much of the original route as posted by the user.

Furthermore, as indicated above, the CE device may access a user's social networking profile to determine if there are locations in an area in which a route is to be determined that a user may wish to pass by during the route (e.g., the model plane example above). Furthermore, present principles recognize that when making such determinations and presenting a route including a location of interest to the user, the CE device in some instances may also present the user with information about the location (e.g. audibly notify the person of the origins of the location and in this respect act as a "tour guide" based on information obtained e.g. from the location's associated website). The CE device may also notify the user that e.g. a location of interest may be upcoming but that it would change the route as originally determined by e.g. adding more distance to the route. Then, e.g., if a user ignores the information or otherwise elects not to go past the location (e.g. the user does not turn where the CE device instructs the user to turn to arrive at the location determined by the CE device to be of interest), the CE device may continue to present the "original" route.

Notwithstanding the foregoing, it is to be understood that in some instances the user may provide input to the CE device of the types and/or categories of locations that a user is interested in passing by while traveling on a route. Thus, for example, the CE device may gather the user's interests from the user's social networking profile, and then present a UI on the CE device for the user to select one or more of the interests for which the CE device should determine if any locations correspond thereto when determining a route. For instance, if the person likes Italian food and model planes (e.g. as indicated in his or her social networking profile), but does not wish to pass by an Italian restaurant while exercising but may wish to pass by a model plane hobby store, the user may provide input indicating as much which the CE device then uses when determining a route in accordance with present principles.

Also in some embodiments, note that person traveling on a route may race against a virtual opponent, where the virtual opponent pace is determined e.g. based on a user's past average pace to encourage the user to beat that past pace, based on e.g. a friend's travel on a similar and even substantially the same route so that the user may race the the friend even if the friend is not present and/or currently traveling the same route, etc. Accordingly, as a user races a virtual opponent around a route, e. a Doppler effect represented by sound (e.g. beeps) may be used to inform the user when the virtual opponent is approaching and/or going away from the user. Then, after completion of the route, e.g. the CE deice may audibly and/or visually indicate the user's finish position relative to the virtual opponent such as e.g. "you beat the virtual opponent by forty seconds."

In yet another aspect, either using a social networking service or using a fitness software application configured for undertaking present principles, a person's route may be compared with the routes of others. This may be done e.g. in real time as one person is traveling the route (or substantially the same route) so that it may he compared to a friends already completed route and provide a "race" where the person currently traveling the route can see the other's virtual progress and thereby race against the other person'position on the route at a time determined to be equivalent relative to starting time of the route. Note that comparing routes In such a way, and even comparing completed routes, may be done e.g. by presenting a user interface with statistics for various categories pertaining to information gathered on the route such as e.g. biometrics, net elevation gain and loss, estimated calories burned, etc. Such comparisons may be based on e.g. the two comparing routes being traveled by people of the same gender, similar ages or the same age group, similar fitness goals, etc.

For completeness, note that as described herein, when route information is provided to a user while traveling the route, this information may be provided audibly through CE device, speakers and/or visually on a display of the CE device, Furthermore, it is to be understood that e.g. audible commands to the CE device may be determined to be commands at the CE device based on e.g. natural language voice/command recognition. Also for completeness, note that while much of the above disclosure is made in reference to exercising such as running and biking, present principles may equally apply to other instances such as routes for e.g. traveling in a motor vehicle, in an airplane, etc. Also note that a user may simply at any point while traveling a route decide to change the parameters of the route, and thus a new and/or derivative of the original route in ay be presented accordingly based on user input of new and/or different parameters.

However, in some embodiments note that alternate routes are not automatically presented always and everywhere when available, and may instead be presented e.g. upon a determination of an obstruction as set forth above and/or upon user request only. Notwithstanding, in some embodiments the user may activate a setting to e.g. cause the CE device to track the route in real time as the user progresses and suggest additional short additions to the route that the user may accept or decline.

Present principles also recognize that e.g. when the CE device receives a request from a user while on route for one or more pieces of the user's own biometric information, the CE device may provide the requested information to the user. Thus, for instance, should the user provide an audible command such as "tell me my heart rate," the CE device may then audibly present the user's current heart rate as detected by a biometric sensor on or in communication with the CE device. However, note that such information may also be periodically presented to the user based on one or more e.g. user-determined settings such as to present the user's heart rate every thirty seconds, every five minutes, etc., and even the current climate conditions such as temperature periodically. Likewise, the CE device may automatically present information when to the user when the terrain changes as the user progresses along the route such as e.g. "you are going up a hill, the top is two hundred yards away."

In addition, when the CE device determines that the route ends at a predetermined distance and/or estimated time, that information may be presented to the user, such as e.g. "push for another thirty seconds, you will be at the end of the route after that," or e.g. "run for another one hundred yards because that is the end of the route." Furthermore, at the completion of a route (e.g. arrival at the ending location), e.g., the CE device may automatically without a user request provide route information to the user and/or biometric information, such as e.g. audibly indicating, "you completed the ten and a half mile route in twenty five minutes and thirty seconds with an average pulse of seventy beats per minute and you are estimated to have burned three hundred forty nine calories."

Furthermore, note that when initially entering parameters for the CE device to determine a route in accordance with present principles, in some instances a UI presented on the CE device may include a selector element that is selectable to "discover" nearby trails and/or exercise routes using the device's current coordinates (e.g. determined using the GPS receiver of the device) and accessing publically available trail information such as from a government website to locate nearby trails that may at least partially form the route.

Last, note that the accessing steps disclosed above may be e.g. accessing of databases of information located in e.g. cloud storage.

While the particular DETERMINING EXERCISE ROUTES BASED ON DEVICE DETERMINED INFORMATION is herein shown and described in detail, it is to be understood that the subject matter which is encompassed by the present invention is limited only by the claims.

What is claimed is:

1. A device comprising:
    at least one computer memory that is not a transitory signal and that comprises instructions executable by at least one processor for;
    receiving first input of terrain information, the terrain information comprising data related to at least one of a desired net elevation gain, a desired net elevation loss, a desired total elevation gain, and a desired total elevation loss;
    accessing map information;
    accessing location information indicating current location of the user;
    receiving second input indicating, a desire for route information;
    responsive to receipt of the second input, determine at least one route based on the location information, the terrain information, and the map information such that the at least one route is determined based at least partially on the terrain information; and
    audibly and/or visually presenting the at least one route at the device.

2. The device of claim 1, wherein the second input includes a hand gesture in free space.

3. The device of claim 1, wherein the instructions are executable for;
    outputting information related to a distance of the at least one route and a time to complete the at least one route, wherein the time to complete the at least one route is based at least partially on at least one past average pace of travel of the user along terrain at least similar to at least some terrain included in the at least one route.

4. The device of claim 1, wherein the instructions are executable for:
    determining plural routes, the plural routes satisfying the second input indicating a desire for route information while remaining within time and/or personal preference constraints of the user.

5. The device of claim 1, wherein the instructions are executable to determine the at least one route based at least in part on at least one time constraint identified based on information in an electronic calendar accessible to the processor and associated with the user.

6. The device of claim 1, wherein the terrain information comprises data at least related to at least one of a desired net elevation gain and a desired net elevation loss.

7. The device of claim 1, wherein the terrain information comprises data at least related to at least one of a desired total elevation gain a desired total elevation loss.

8. The device of claim 1, wherein the instructions are executable for:
    receiving third input comprising information indicating a maximum radius from a starting location that the user desires to travel; and
    determine the at least one route based on the location information, the terrain information, the map information, and the information indicating the maximum radius such that the at least one route is determined based at least partially on the terrain information and the information indicating the maximum radius.

9. The device of claim 4, wherein the instructions are executable for:
    presenting a user interface (UI) on a display accessible to the at least one processor, the UI presenting information related to the plural routes.

10. The device of claim 9, wherein the UI presents graphical representations respectively associated with at least two of the plural routes.

11. The device of claim 10, wherein each of the graphical representations are respectively selectable to audibly and/or visually present at the device the respectively associated route.

12. The device of claim 9, wherein the UI presents text setting forth a comparison of the plural routes to each other.

13. The device of claim 9, wherein the UI presents information related to at least one of respective difficulties of the plural routes and respective estimated calories to be expended on the plural routes.

* * * * *